US008029511B2

(12) United States Patent
Bowman et al.

(10) Patent No.: US 8,029,511 B2
(45) Date of Patent: Oct. 4, 2011

(54) MULTI-STAGE BIOMATERIAL INJECTION SYSTEM FOR SPINAL IMPLANTS

(75) Inventors: Bruce R. Bowman, Eden Prairie, MN (US); Rob Kohler, Lake Elmo, MN (US); Erik Martz, Savage, MN (US); Dan Melink, Prior Lake, MN (US); Khin Myint, Shakopee, MN (US); Michael Ahrens, Neustadt I.H. (DE); Jean-Charles Lehuec, Pessac (FR); John Sherman, Wayzata, MN (US); Scott Hook, Edina, MN (US); Dennis Johnson, Shakopee, MN (US); Qi-Bin Bao, Marquette, MI (US); Robert Garryl Hudgins, Burnsville, MN (US)

(73) Assignee: Disc Dynamics, Inc., Eden Prairie, MN (US)

( * ) Notice: Subject to any disclaimer, the term of this patent is extended or adjusted under 35 U.S.C. 154(b) by 1895 days.

(21) Appl. No.: 10/984,493

(22) Filed: Nov. 9, 2004

(65) Prior Publication Data
US 2005/0209601 A1    Sep. 22, 2005

Related U.S. Application Data

(60) Provisional application No. 60/555,382, filed on Mar. 22, 2004.

(51) Int. Cl.
*A61B 17/58* (2006.01)
*A61B 17/60* (2006.01)
*A61F 2/00* (2006.01)
(52) U.S. Cl. ......................................................... 606/92
(58) Field of Classification Search ................ 623/17.11, 623/17.12; 606/92, 90
See application file for complete search history.

(56) References Cited

U.S. PATENT DOCUMENTS

| 4,834,757 | A |   | 5/1989 | Brantigan |
| 5,021,046 | A | * | 6/1991 | Wallace ............... 604/97.03 |
| 5,047,055 | A |   | 9/1991 | Bao et al. |
| 5,342,298 | A | * | 8/1994 | Michaels et al. ........... 604/65 |
| 5,425,772 | A |   | 6/1995 | Brantigan |
| 5,449,345 | A | * | 9/1995 | Taylor et al. ............ 604/100.03 |

(Continued)

FOREIGN PATENT DOCUMENTS

DE    3922203 C1    10/1990

(Continued)

OTHER PUBLICATIONS

Sato et al., "An Experimental Study of the Regeneration of the Intervertebral Disc With an Allograft of Cultured Annulus Fibrosus Cells Using a Tissue-Engineering Method", *Spine*, 2003, pp. 548-553, vol. 28, No. 6, Lippincott Williams & Wilkins, Inc.

(Continued)

*Primary Examiner* — Thomas C. Barrett
*Assistant Examiner* — David Bates
(74) *Attorney, Agent, or Firm* — Stoel Rives LLP

(57) ABSTRACT

A method and apparatus for fluidly coupling a reservoir containing a flowable biomaterial to a mold. The flow of the flowable biomaterial into the mold is controlled in accordance with a first operating parameter. At least one injection condition is monitored. The flow of the flowable biomaterial is controlled in accordance with a second operating parameter in response to one or more of the injection conditions reaching a threshold level. The second operating parameter is maintained during at least a portion of the curing of the flowable biomaterial. In some embodiments, the second operating parameter may optionally include permitting a portion of the flowable biomaterial to be expelled from the mold.

53 Claims, 13 Drawing Sheets

U.S. PATENT DOCUMENTS

| | | | |
|---|---|---|---|
| 5,459,700 A | 10/1995 | Jacobs | |
| 5,460,609 A | 10/1995 | O'Donnell | |
| 5,556,429 A | 9/1996 | Felt | |
| 5,562,614 A * | 10/1996 | O'Donnell | 604/65 |
| 5,562,621 A | 10/1996 | Claude et al. | |
| 5,599,301 A * | 2/1997 | Jacobs et al. | 604/65 |
| 5,704,912 A * | 1/1998 | Lawrence et al. | 604/97.02 |
| 5,795,353 A | 8/1998 | Felt | |
| 5,797,679 A | 8/1998 | Grulke et al. | |
| 5,827,289 A | 10/1998 | Reiley et al. | |
| 5,888,220 A | 3/1999 | Felt et al. | |
| 5,951,563 A * | 9/1999 | Brown | 606/92 |
| 6,042,262 A | 3/2000 | Hajianpour | |
| 6,048,346 A | 4/2000 | Reiley et al. | |
| 6,066,154 A | 5/2000 | Reiley et al. | |
| 6,079,868 A | 6/2000 | Rydell | |
| 6,140,452 A | 10/2000 | Felt et al. | |
| 6,187,048 B1 | 2/2001 | Milner et al. | |
| 6,203,759 B1 * | 3/2001 | Pelc et al. | 422/100 |
| 6,224,630 B1 | 5/2001 | Bao et al. | |
| 6,240,926 B1 | 6/2001 | Chin Gan et al. | |
| 6,248,131 B1 | 6/2001 | Felt et al. | |
| 6,254,569 B1 | 7/2001 | O'Donnell et al. | |
| 6,264,659 B1 | 7/2001 | Ross et al. | |
| 6,280,456 B1 | 8/2001 | Scribner et al. | |
| 6,306,177 B1 | 10/2001 | Felt et al. | |
| 6,402,784 B1 | 6/2002 | Wardlaw | |
| 6,416,776 B1 | 7/2002 | Shamie | |
| 6,443,988 B2 | 9/2002 | Felt et al. | |
| 6,468,279 B1 | 10/2002 | Reo | |
| 6,575,919 B1 | 6/2003 | Reiley et al. | |
| 6,602,291 B1 | 8/2003 | Ray et al. | |
| 6,607,544 B1 | 8/2003 | Boucher et al. | |
| 6,623,505 B2 | 9/2003 | Scribner et al. | |
| 6,641,587 B2 | 11/2003 | Scribner et al. | |
| 6,645,213 B2 | 11/2003 | Sand et al. | |
| 6,692,563 B2 | 2/2004 | Zimmermann | |
| 6,719,761 B1 | 4/2004 | Reiley et al. | |
| 6,719,773 B1 | 4/2004 | Boucher et al. | |
| 6,733,505 B2 | 5/2004 | Li | |
| 6,814,763 B2 | 11/2004 | Bechtold et al. | |
| 6,889,719 B2 | 5/2005 | Watanabe et al. | |
| 6,908,506 B2 | 6/2005 | Zimmermann | |
| 6,979,341 B2 | 12/2005 | Scribner et al. | |
| 2002/0029083 A1 | 3/2002 | Zucherman et al. | |
| 2002/0077701 A1 | 6/2002 | Kuslich | |
| 2002/0165542 A1 | 11/2002 | Ferree | |
| 2002/0173851 A1 | 11/2002 | McKay | |
| 2002/0189622 A1 | 12/2002 | Cauthen, III et al. | |
| 2003/0040800 A1 | 2/2003 | Li et al. | |
| 2003/0045937 A1 | 3/2003 | Ginn | |
| 2003/0195628 A1 * | 10/2003 | Bao et al. | 623/17.12 |
| 2003/0199984 A1 | 10/2003 | Trieu | |
| 2003/0220649 A1 * | 11/2003 | Bao et al. | 606/90 |
| 2004/0034427 A1 | 2/2004 | Goel et al. | |
| 2004/0091540 A1 | 5/2004 | Desrosiers et al. | |
| 2004/0097927 A1 | 5/2004 | Yeung et al. | |
| 2004/0260238 A1 * | 12/2004 | Call | 604/97.03 |
| 2005/0209602 A1 | 9/2005 | Bowman et al. | |
| 2006/0247657 A1 | 11/2006 | Trieu | |
| 2007/0112299 A1 | 5/2007 | Smit et al. | |
| 2007/0173943 A1 | 7/2007 | Dulak et al. | |

FOREIGN PATENT DOCUMENTS

| | | |
|---|---|---|
| DE | 100 24 922 C 1 | 1/2002 |
| FR | 2639823 | 12/1988 |
| WO | WO 97/26847 | 7/1997 |
| WO | WO 99/04720 | 2/1999 |
| WO | WO 01-32100 A2 | 5/2001 |
| WO | WO 2004030528 A1 * | 4/2004 |

OTHER PUBLICATIONS

U.S. Appl. No. 11/268,786, filed Nov. 8, 2005, Myinl et al.
U.S. Appl. No. 11/268,556, flied Nov. 8, 2005, Lehuec et al.
U.S. Appl. No. 11/268,876, filed Nov. 8, 2005, Carter et al.
U.S. Appl. No. 11/304,053, flied Dec. 15, 2005, Yuan et al.
O.L. Osti, et al, "Annular Tears and Disc Degeneration in the Lumbar Spine," *The Journal of Bone and Joint Surgery*, vol. 74-B(5), (Sep. 1992), pp. 678-682, jointly published in London, England and Boston, Massachusetts.
O.L. Osti, et al, "Anulus Tears and Intervertebral Disc Degeneration, An Experimental Study Using an Animal Model," *Spine*, vol. 15, No. 8, (1990), pp. 762-767, J.B. Lippincott Company, Philadelphia, Pennsylvania.
P. Kambin, et al., "Development of Degenerative Spondylosis of the Lumbar Spine after Partial Discetomy, *Spine*," vol. 20, No. 5 (1995), pp. 599-607, J.B. Lippincott Company, Philadelphia, Pennsylvania.

* cited by examiner

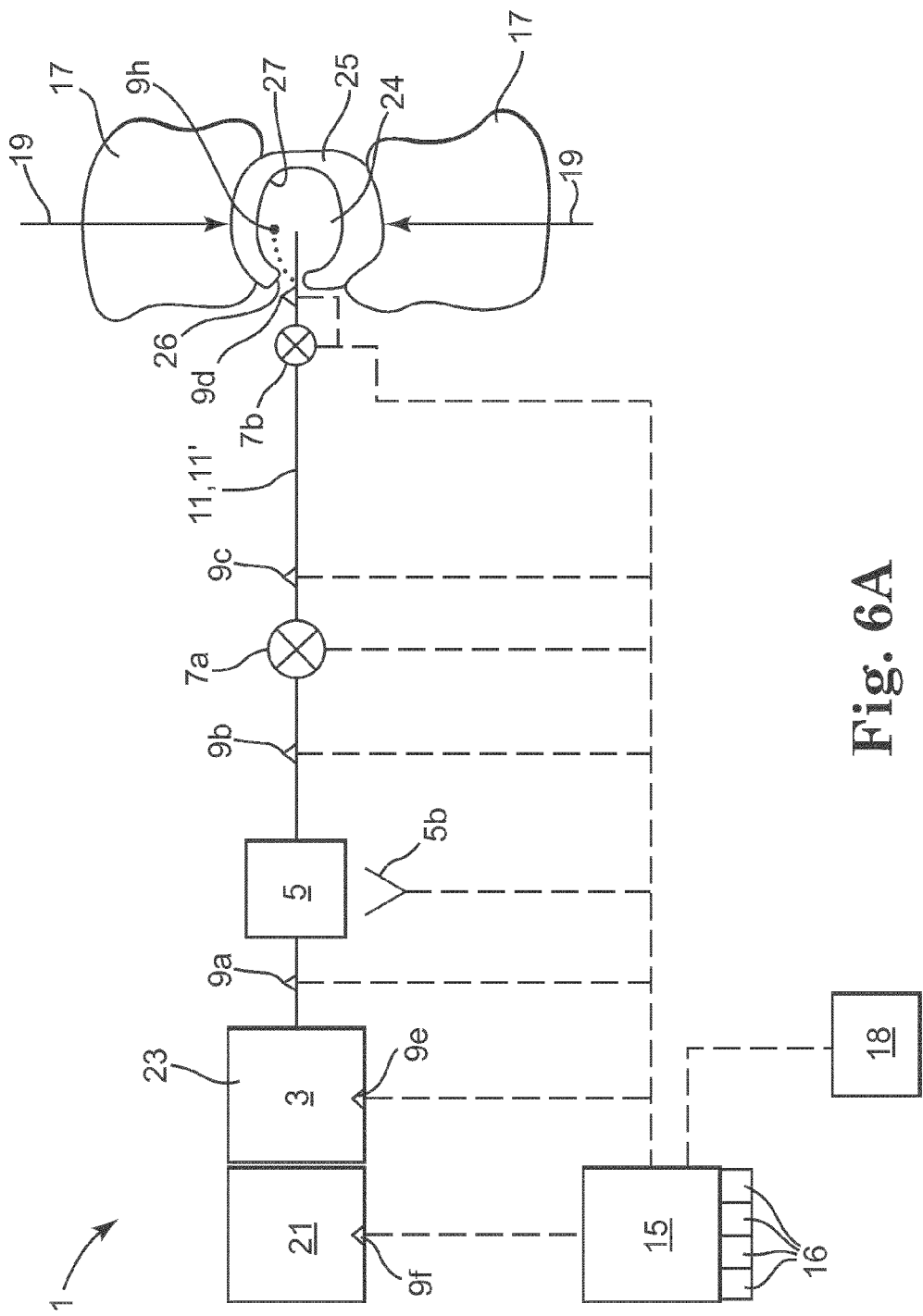

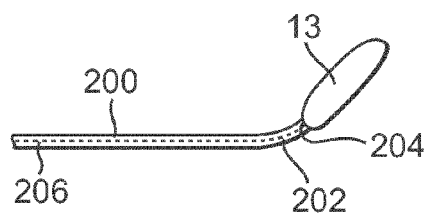
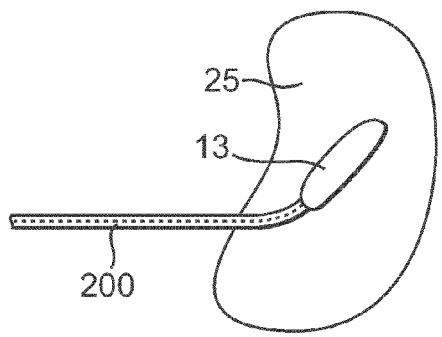
Fig. 16A
Fig. 16B
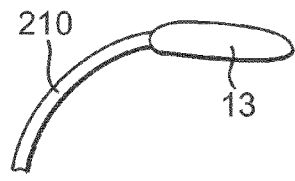
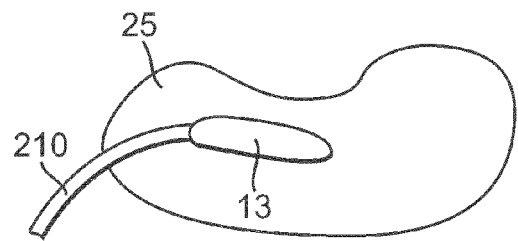
Fig. 17A
Fig. 17B
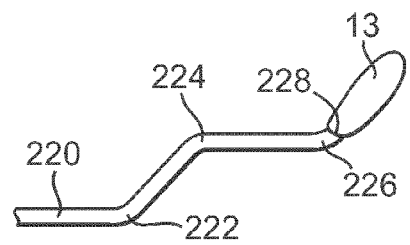
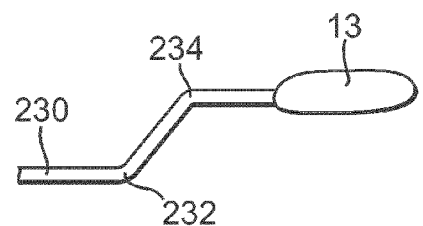
Fig. 18
Fig. 19

MULTI-STAGE BIOMATERIAL INJECTION SYSTEM FOR SPINAL IMPLANTS

The present application claims the benefit of U.S. Provisional Application Ser. No. 60/555,382 entitled MULTI-STAGE BIOMATERIAL INJECTION SYSTEM FOR SPINAL IMPLANTS filed on Mar. 22, 2004.

FIELD OF THE INVENTION

The present invention relates to a method and apparatus for filling an intervertebral disc space with an in situ curable biomaterial using a biomaterial injection system to form an implant device and to a method for replacing, in whole or in part, an intervertebral disc using the present method and apparatus.

BACKGROUND OF THE INVENTION

The intervertebral discs, which are located between adjacent vertebrae in the spine, provide structural support for the spine as well as the distribution of forces exerted on the spinal column. An intervertebral disc consists of three major components: cartilage endplates, nucleus pulpous, and annulus fibrosus. The central portion, the nucleus pulpous or nucleus, is relatively soft and gelatinous; being composed of about 70 to 90% water. The nucleus pulpous has a high proteoglycan content and contains a significant amount of Type II collagen and chondrocytes. Surrounding the nucleus is the annulus fibrosus, which has a more rigid consistency and contains an organized fibrous network of approximately 40% Type I collagen, 60% Type II collagen, and fibroblasts. The annular portion serves to provide peripheral mechanical support to the disc, afford torsional resistance, and contain the softer nucleus while resisting its hydrostatic pressure.

Intervertebral discs, however, are susceptible to a number of injuries. Disc herniation occurs when the nucleus begins to extrude through an opening in the annulus, often to the extent that the herniated material impinges on nerve roots in the spine or spinal cord. The posterior and posterio-lateral portions of the annulus are most susceptible to attenuation or herniation, and therefore, are more vulnerable to hydrostatic pressures exerted by vertical compressive forces on the intervertebral disc. Various injuries and deterioration of the intervertebral disc and annulus fibrosus are discussed by Osti et al., Annular Tears and Disc Degeneration in the Lumbar Spine, *J. Bone and Joint Surgery*, 74-B(5), (1982) pp. 678-682; Osti et al., Annulus Tears and Intervertebral Disc Degeneration, *Spine,* 15(8) (1990) pp. 762-767; Kamblin et al., Development of Degenerative Spondylosis of the Lumbar Spine after Partial Discectomy, *Spine*, 20(5) (1995) pp. 599-607.

Many treatments for intervertebral disc injury have involved the use of nuclear prostheses or disc spacers. A variety of prosthetic nuclear implants are known in the art. For example, U.S. Pat. No. 5,047,055 (Bao et al.) teaches a swellable hydrogel prosthetic nucleus. Other devices known in the art, such as intervertebral spacers, use wedges between vertebrae to reduce the pressure exerted on the disc by the spine. Intervertebral disc implants for spinal fusion are known in the art as well, such as disclosed in U.S. Pat. No. 5,425,772 (Brantigan) and U.S. Pat. No. 4,834,757 (Brantigan).

Further approaches are directed toward fusion of the adjacent vertebrate, e.g., using a cage in the manner provided by Sulzer. Sulzer's BAK® Interbody Fusion System involves the use of hollow, threaded cylinders that are implanted between two or more vertebrae. The implants are packed with bone graft to facilitate the growth of vertebral bone. Fusion is achieved when adjoining vertebrae grow together through and around the implants, resulting in stabilization.

Apparatuses and/or methods intended for use in disc repair have also been described but none appear to have been further developed, and certainly not to the point of commercialization. See, for instance, French Patent Appl. No. FR 2 639 823 (Garcia) and U.S. Pat. No. 6,187,048 (Milner et al.). Both references differ in several significant respects from each other and from the apparatus and method described below. For instance, neither reference teaches switching the flow of biomaterial between discrete operating parameters or methods of detecting ruptures in the mold. Further, neither reference teaches shunting an initial portion of a curing biomaterial in the course of delivering the biomaterial to the disc space.

Prosthetic implants formed of biomaterials that can be delivered and cured in situ, using minimally invasive techniques to form a prosthetic nucleus within an intervertebral disc have been described in U.S. Pat. No. 5,556,429 (Felt) and U.S. Pat. No. 5,888,220 (Felt et al.), and U.S. Patent Publication No. US 2003/0195628 (Felt et al.), the disclosures of which are incorporated herein by reference. The disclosed method includes, for instance, the steps of inserting a collapsed mold apparatus (which in a preferred embodiment is described as a "mold") through an opening within the annulus, and filling the mold to the point that the mold material expands with a flowable biomaterial that is adapted to cure in situ and provide a permanent disc replacement. Related methods are disclosed in U.S. Pat. No. 6,224,630 (Bao et al.), entitled "Implantable Tissue Repair Device" and U.S. Pat. No. 6,079,868 (Rydell), entitled "Static Mixer".

BRIEF SUMMARY OF THE INVENTION

The present invention relates to a method and apparatus for filling an intervertebral disc space with an in situ curable biomaterial. The biomaterial injection system can be used, for example, to implant a prosthetic total disc, or a prosthetic disc nucleus, in a manner that leaves the surrounding disc tissue substantially intact. The phrase intervertebral disc prosthesis is used generically to refer to both of these variations. Optionally, the device and system of the invention are adapted for minimally invasive use. Various implant procedures, implant molds, and biomaterials related to intervertebral disc replacement suitable for use with the present invention are disclosed in U.S. Pat. No. 5,556,429 (Felt); U.S. Pat. No. 6,306,177 (Felt, et al.); U.S. Pat. No. 6,248,131 (Felt, et al.); U.S. Pat. No. 5,795,353 (Felt); U.S. Pat. No. 6,079,868 (Rydell); U.S. Pat. No. 6,443,988 (Felt, et al.); U.S. Pat. No. 6,140,452 (Felt, et al.); U.S. Pat. No. 5,888,220 (Felt, et al.); U.S. Pat. No. 6,224,630 (Bao, et al.), and U.S. patent application Ser. Nos. 10/365,868 and 10/365,842, all of which are hereby incorporated by reference.

The present method of filling an intervertebral disc space with a flowable biomaterial includes the step of fluidly coupling a reservoir containing the flowable biomaterial to the intervertebral disc space. The delivery of the flowable biomaterial into the intervertebral disc space is controlled in accordance with a first operating parameter. At least one injection condition is monitored. The delivery of the flowable biomaterial is controlled in accordance with a second operating parameter in response to one or more of the injection conditions reaching a threshold level. The second operating parameter is maintained during at least a portion of the curing of the flowable biomaterial.

In one embodiment, the method includes fluidly coupling the reservoir containing the flowable biomaterial to a mold located in the intervertebral disc space. The first operating parameter delivers the flowable biomaterial to the mold so that the mold substantially fills the intervertebral disc space.

In another embodiment, a predetermined period of time is permitted to lapse after the at least one injection condition reaches the threshold level before initiating the second operating parameter. This dwell time comprises a third operating parameter. The length of this dwell time can be fixed or can vary from patient-to-patient.

The first operating parameter preferably applies sufficient pressure to rapidly fill the mold and to expand the mold to fill the disc space. A first injection condition triggers a second operating parameter, which maintains adequate pressure for a certain dwell time to completely fill the disc space and to distract the intervertebral disc space. Following the dwell time, a third operating parameter optionally permits a portion of the flowable biomaterial to be expelled from the intervertebral disc space, followed by a second dwell time that continues until the biomaterial adequately cures.

The present method optionally includes pretreating the flowable biomaterial. The biomaterial can also be exposed to ultraviolet light, heating and/or mixed prior to delivery to the intervertebral disc space.

In one embodiment, the flow of biomaterial is directed away from the intervertebral disc space until a predetermined quantity of biomaterial is delivered to a chamber in a purge device. In one embodiment, the first operating parameter includes the step of applying a first operating pressure to the flowable biomaterial in the reservoir and applying a second operating pressure, lower than the first operating pressure, to the flowable biomaterial in the reservoir. In another embodiment the intervertebral disc space exerts a pressure on the flowable biomaterial in the intervertebral disc space greater than the second operating pressure.

The step of monitoring at least one injection condition typically includes monitoring the pressure of the flowable biomaterial between the reservoir and the intervertebral disc space and/or the pressure of the flowable biomaterial in the intervertebral disc space. The step of monitoring at least one injection condition can be monitoring at least one of the pressure, the flow rate, elapsed time, or the total volume of the flowable biomaterial flowing between the reservoir and the intervertebral disc space.

The present method also includes the step of recording data corresponding to at least one of the injection conditions during the flow of flowable biomaterial. The injection condition data is optionally uploaded to a computer. The present method also includes determining whether any of the injection conditions is in an out of specification condition and indicating an out of specification condition. Alternatively, the flow of biomaterial is altered and/or the biomaterial is withdrawn from the intervertebral disc space in response to an out of specification condition.

The flow of flowable biomaterial can be manually switched to the second operating parameter in response to one or more of the injection conditions reaching a threshold level or automatically switched by a controller. The present method optionally includes adjusting the threshold level as a function of patient parameters. The first and second operating parameter typically comprises a plurality of variables, such as for example, injection pressure, biomaterial temperature, and the like.

The present method also includes positioning an evaluation mold in the intervertebral disc space prior to the delivery of the biomaterial. A liquid is delivered to the evaluation mold so that the mold substantially fills the intervertebral disc space and measurements, such as for example disc height, pressure, and the like, are taken. The liquid is removed from the evaluation mold and the volume of liquid injected and/or removed is measured. The evaluation mold is then removed from the intervertebral disc space. The liquid is preferably delivered under pressure sufficient to distract the intervertebral disc space. The liquid and/or the evaluation mold optionally have radiopaque properties. The present invention also includes use of the present biomaterial injection system to control delivery and/or removal of the liquid to the evaluation mold.

In the preferred embodiment, imaging can be used to measure the distraction of the intervertebral disc space, to evaluate whether the mold substantially fills the intervertebral disc space, to evaluate the geometry of the intervertebral disc space, and/or to supply information to the surgeon regarding adequacy of the nucleus removal. The evaluation mold can either be positioned in the implant mold, directly in the annulus, or within the disc space in the case of complete disc removal. In another embodiment, the intervertebral disc space containing the evaluation mold and the liquid is imaged and at least one of the first operating parameter and/or the second operating parameter are established based on the imaging of the intervertebral disc space. In one embodiment, the intervertebral disc space is imaged to estimate the volume of biomaterial required. That estimate can then be compared to the amount of liquid removed from the evaluation mold.

In another embodiment, a liquid is delivered under pressure to the evaluation mold sufficient to distract the intervertebral disc space. The volume of liquid in the evaluation mold may be held constant for a period of time. Additional liquid is added to the evaluation mold when the pressure in the mold drops to a predetermined level. The steps of delivering, holding and adding additional liquid is preferably repeated a plurality of cycles.

In another embodiment, a liquid is continuously delivered to the evaluation mold at a constant pressure. The rate at which the liquid is delivered to the evaluation mold is measured. The compliance of the intervertebral disc space is measured as a function of the rate of change of the delivery of liquid.

The present method also includes positioning a guide wire in the mold and imaging the intervertebral disc space containing the guide wire. The guide wire optionally includes an imaging target.

The present method also includes positioning a radiopaque sheath over the mold before the delivery of the biomaterial. The intervertebral disc space containing the radiopaque sheath is imaged and the radiopaque sheath is removed before delivering the biomaterial.

The present invention is also directed to an apparatus adapted to deliver a flowable biomaterial to an intervertebral disc space. The apparatus includes a reservoir containing the flowable biomaterial fluidly coupled to the intervertebral disc space, at least one sensor adapted to monitor at least one injection condition of the flowable biomaterial, and a controller. The controller is programmed to monitor the at least one sensor and to control the flow of the flowable biomaterial into the mold in accordance with a first operating parameter. In response to one or more of the injection conditions reaching a threshold level, the controller controls the flow of the flowable biomaterial in accordance with a second operating parameter and maintains the second operating parameter during a certain time period or dwell time before switching to the third operating parameter and maintaining the third operating parameter during at least a portion of the curing of the flowable biomaterial.

In one embodiment, the apparatus includes a mold located in the intervertebral disc space fluidly coupled to the reservoir containing the flowable biomaterial. The controller is programmed so that the first operating parameter delivers the flowable biomaterial to the mold so that the mold substantially fills the intervertebral disc space.

In one embodiment, the controller is programmed to initiate a second operating parameter during which the system waits a predetermined period of time after the first operating parameter (i.e., the at least one injection condition reaches the threshold level at a second operating parameter) before initiating the third operating parameter. In another embodiment, the controller is programmed to deliver the flowable biomaterial in accordance with a third operating parameter that maintains the flowable biomaterial at a predetermined pressure in the intervertebral disc space for a predetermined period of time after the at least one injection condition reaches the threshold level and before the second operating parameter. Operating parameters can be linear, non-linear, continuous, discontinuous, or any other configuration necessary to achieve the desired injection profile. The operating parameter can also be modified real-time based on feedback from the sensors monitoring the injection conditions.

The controller is preferably programmed so that the first operating parameter comprises a pressure sufficient to distract the intervertebral disc space. In another embodiment, the controller is programmed so that the second operating parameter permits a portion of the flowable biomaterial to be expelled from the intervertebral disc space. The controller is also optionally programmed to control pretreatment of the flowable biomaterial.

The apparatus optionally includes a source of ultraviolet light and/or heating directed at the flowable biomaterial prior to delivery to the intervertebral disc space. The present apparatus also optionally includes a mixing device located between the reservoir of flowable biomaterial and the intervertebral disc space. The present apparatus also optionally includes a purging device adapted to direct a predetermined quantity of the flow of biomaterial away from the intervertebral disc space.

In one embodiment, the controller is programmed so that the second operating parameter applies a second operating pressure to the biomaterial in the reservoir that is lower than the first operating pressure applied under the first operating parameter. The controller can monitor the pressure of the flowable biomaterial between the reservoir and the intervertebral disc space and or in the intervertebral disc space. The controller is preferably programmed to monitor at least one injection condition comprises monitoring at least one of the pressure, the flow rate, elapsed time, or the total volume of the flowable biomaterial flowing between the reservoir and the intervertebral disc space.

The controller is preferably programmed to record data corresponding to at least one of the injection conditions during the flow of flowable biomaterial. In one embodiment, the controller is programmed to upload to a computer data corresponding to at least one of the injection conditions recorded during the flow of flowable biomaterial.

The controller may also be programmed to determine whether the at least one injection condition comprises an out of specification condition and to indicate an out of specification condition. Alternatively, the controller is programmed to alter the flow of flowable biomaterial or to withdraw at least a portion of the biomaterial from the intervertebral disc space in response to an out of specification condition.

The controller preferably adjusts the threshold level as a function of patient parameters. The first, second and third operating parameters typically comprises a plurality of variable.

The present invention may also include an evaluation mold adapted to be positioned in the intervertebral disc space prior to the delivery of the biomaterial and a liquid adapted to be delivered to the evaluation mold so that the mold substantially fills the intervertebral disc space. The controller is preferably programmed to remove the liquid from the evaluation mold and to measure the amount of liquid removed from the evaluation mold. The liquid and/or the evaluation mold optionally have radiopaque properties.

In one embodiment, the controller is programmed to estimate the volume of biomaterial required to fill the intervertebral disc space and to compare the amount of liquid removed from the evaluation mold with an estimated volume of the intervertebral disc space measured using imaging techniques.

In another embodiment, the controller is programmed to deliver a liquid under pressure to the evaluation mold sufficient to distract the intervertebral disc space, to hold the volume of liquid in the evaluation mold constant for a period of time, and to add additional liquid to the evaluation mold when the pressure in the mold drops to a predetermined level. The controller is preferably programmed to repeat the steps a plurality of cycles and estimate the compliance of the intervertebral disc space or spinal unit. In one embodiment, the operating parameters are modified in response to the estimate of compliance.

In another embodiment, the controller is programmed to continuously deliver a liquid to the evaluation mold at a constant pressure, to measure the rate at which the liquid is delivered to the evaluation mold, and to estimate the compliance of the intervertebral disc space as a function of the changing rate at which the liquid is delivered.

In one embodiment, the present invention includes a guide wire positioned in the mold. In another embodiment, a radiopaque sheath is positioned over the mold.

The present invention is also directed to a controller programmed to determine whether at least one injection condition comprises an out of specification condition and to generate a signal of the out of specification condition.

The present invention is also directed to an apparatus adapted to deliver a flowable biomaterial to a mold located in an intervertebral disc space. The apparatus includes a reservoir containing the flowable biomaterial fluidly coupled to the mold, an actuator providing a flow of the flowable biomaterial into the mold in accordance with a first operating parameter and at least one sensor monitoring at least one operating parameter of the flowable biomaterial. The apparatus also includes a display adapted to indicate that the at least one injection condition has reached a threshold level and a switch that controls the flow the flowable biomaterial in accordance with a second operating parameter.

As used herein the following words and terms shall have the meanings ascribed below:

"biomaterial" will generally refer to a material that is capable of being introduced to the site of a joint and cured to provide desired physical-chemical properties in vivo. In one embodiment the term will refer to a material that is capable of being introduced to a site within the body using minimally invasive mechanism, and cured or otherwise modified in order to cause it to be retained in a desired position and configuration. Generally such biomaterials are flowable in their uncured form, meaning they are of sufficient viscosity to allow their delivery through a delivery tube of on the order of about 1 mm to about 6 mm inner diameter, and preferably of about 2 mm to about 3 mm inner diameter. Such biomaterials are also curable, meaning that they can be cured or otherwise modified, in situ, at the tissue site, in order to undergo a phase or chemical change sufficient to retain a desired position and configuration;

"cure" and inflections thereof, will generally refer to any chemical transformation (e.g., reacting or cross-linking), physical transformation (e.g., hardening or setting), and/or mechanical transformation (e.g., drying or evaporating) that allows the biomaterial to change or progress from a first physical state or form (generally liquid or flowable) that allows it to be delivered to the site, into a more permanent second physical state or form (generally solid) for final use in vivo. When used with regard to the method of the invention, for instance, "curable" can refer to uncured biomaterial, having the potential to be cured in vivo (as by catalysis or the application of a suitable energy source), as well as to the biomaterial in the process of curing. As further described herein, in selected embodiments the cure of a biomaterial can generally be considered to include three stages, including (a) the onset of gelation, (b) a period in which gelation occurs and the biomaterial becomes sufficiently tack-free to permit shaping, and (c) complete cure to the point where the biomaterial has been finally shaped for its intended use. "minimally invasive mechanism" refers to a surgical mechanism, such as microsurgical, percutaneous, or endoscopic or arthroscopic surgical mechanism, that can be accomplished with minimal disruption of the pertinent musculature, for instance, without the need for open access to the tissue injury site or through minimal incisions (e.g., incisions of less than about 4 cm and preferably less than about 2 cm). Such surgical mechanism are typically accomplished by the use of visualization such as fiberoptic or microscopic visualization, and provide a post-operative recovery time that is substantially less than the recovery time that accompanies the corresponding open surgical approach;

"mold" will generally refer to the portion or portions of an apparatus of the invention used to receive, constrain, shape and/or retain a flowable biomaterial in the course of delivering and curing the biomaterial in situ. A mold may include or rely upon natural tissues (such as the annular shell of an intervertebral disc) for at least a portion of its structure, conformation or function. The mold, in turn, is responsible, at least in part, for determining the position and final dimensions of the cured prosthetic implant. As such, its dimensions and other physical characteristics can be predetermined to provide an optimal combination of such properties as the ability to be delivered to a site using minimally invasive mechanism, filled with biomaterial, prevent moisture contact, and optionally, then remain in place as or at the interface between cured biomaterial and natural tissue. In one embodiment the mold material can itself become integral to the body of the cured biomaterial. The mold can be elastic or inelastic, permanent or bio-reabsorbable.

BRIEF DESCRIPTION OF THR SEVERAL VIEWS OF THE DRAWING

FIG. 6A is a schematic illustration of an alternate method and apparatus of the present invention.

FIGS. 16A-16B illustrate an alternate delivery tube for posterior access into the annulus in accordance with the present invention.

FIGS. 17A-17B illustrate an alternate delivery tube for lateral access into the annulus in accordance with the present invention.

FIG. 18 illustrates an alternate delivery tube in accordance with the present invention.

FIG. 19 illustrates another alternate delivery tube in accordance with the present invention.

DETAILED DESCRIPTION OF THE INVENTION

Figure 1:
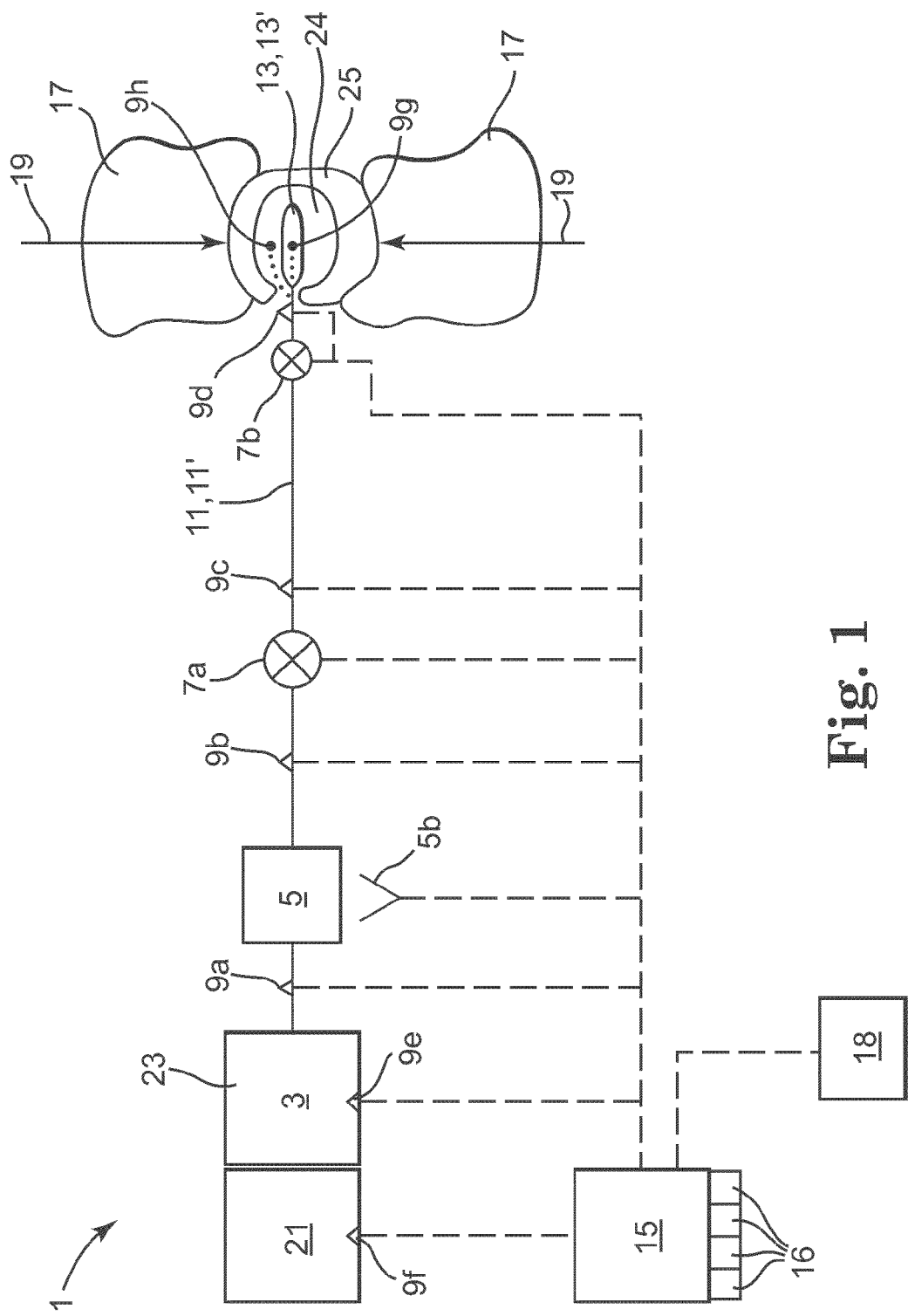
FIG. 1 is a schematic illustration of the method and apparatus of the present invention.

FIG. 1 illustrates one embodiment of a biomaterial injection system 1 in accordance with the present invention. The biomaterial injection system 1 includes a reservoir 3 containing the biomaterial 23 fluidly coupled to an implant mold 13 by a delivery tube 11. The deflated implant mold 13 is dimensioned to be positioned within the intervertebral disc space 19. The mold is filled with uncured biomaterial 23 in order to provide a replacement disc. As the biomaterial 23 is delivered to the implant mold 13, the mold 13 expands to substantially fill the intervertebral disc space 19, and in particular, fill the cavity 24 formed in the annulus 25 as a result of removal of some or all of the nucleus.

Intervertebral disc space refers generally to the space between adjacent vertebrae. The embodiments illustrated herein are equally applicable to both a complete disc replacement and to a full or partial nucleus replacement. A replacement disc refers to both a complete disc replacement and to a full or partial nucleus replacement.

The reservoir 3 is adapted to hold the biomaterial 23, and in some embodiments, the reservoir 3 heats and/or mixes the biomaterial 23. In some embodiments, the biomaterial 23 is pretreated before use. The biomaterial 23 can either be pretreated before being placed in the reservoir 3 or the pretreatment can be performed in the reservoir 3. For example, the biomaterial 23 can be heated, mechanically agitated, or both, such as heating in a rotating oven before being placed in the reservoir 3. For some polyurethane biomaterials, for example, sealed packages of biomaterial 23 are heated while rotating in an oven at about 75° C. for about 3 hours, maintained at 75° C. degrees C. without rotating for an additional 3 hours, and then kept in the oven at about 37° C. until surgical implantation. During the second 3 hour period, the package of biomaterial 23 is preferably retained in the oven without rotating and in an upright position during heating so that bubbles rise to the top. The flowable biomaterial 23 containing the bubbles is preferably purged before it reaches the mold, as will be discussed below.

A chamber 5 is optionally located in-line between the reservoir 3 and the mold 13. The chamber 5 can be used to heat, mix and/or stage the biomaterial 23. In some embodiments, the chamber 5 can be used to initiate curing of the biomaterial 23, such as for example by exposing the biomaterial 23 to an ultraviolet light source or a heat source 5b.

An actuator 21 is mechanically coupled to the reservoir to expel the biomaterial 23 from the reservoir 3 and into the delivery tube 11. The actuator 21 can be a pneumatic or hydraulic cylinder, a mechanical drive such as an electric motor with a ball screw, a drive screw or belt, or a variety of other mechanisms well know to those of skill in the art. Control of the actuator 21 is typically the primary operating parameter used to create the desired injection profile. Other possible operating parameters that can be controlled by the controller 15 include releasing biomaterial 23 through one or more of the purge devices 7a, 7b, biomaterial temperature, biomaterial viscosity, and the like.

As used herein, "operating parameter" refers to one or more independent variables that can be controlled during the injection of biomaterial.

The operating parameters can be linear, non-linear, continuous, discontinuous, or any other configuration necessary to achieve the desired injection profile. The operating parameter can also be modified real-time based on feedback from the sensors monitoring the injection conditions. For example, a control algorithm, such as Proportional Integral Derivative (PID) control, can be used to evaluate the injection condition data in light of the desired injection profile.

For embodiments where the actuator 21 is a pneumatic cylinder, it should be noted that many hospitals and clinics do not have sources of compressed air greater than 50 pounds per square inch (hereinafter "psi"). Thus, in some embodiments the pneumatic cylinder needs to magnify the available compressed air source by a factor of about 3. Thus, an initial pressure of about 50 psi becomes about 150 psi in the reservoir 3.

The delivery tube 11 preferably includes at least one purge device 7a. In the illustrated embodiment, the purge device 7a is located downstream of the chamber 5. In another embodiment, a secondary purge device 7b is located closer to the mold 13. The purge devices 7a and 7b are referred to collectively as "7". Suitable purge devices can include but are not limited to, reservoirs, three-way valve systems, and the like. The purge devices 7 can divert or redirect the flow of biomaterial 23 aside in order to purge a portion, which can include an initial portion that may be inadequately mixed or contain bubbles. The purge devices 7 can also be employed if there is a system failure, such as rupture of a mold 13, to quickly divert biomaterial from the intervertebral disc space.

The purge devices 7a, 7b can be operated manually or automatically. In the preferred embodiment one or both are operated by controller 15 and/or using the mechanism in FIGS. 4 and 5. In one embodiment, the purge device 7a is operated manually by the surgical staff and the purge device 7b is operated by the controller 15.

In the illustrated embodiment, the biomaterial injection system 1 preferably includes one or more sensors 9a, 9b, 9c, 9d, 9e, 9f, 9g and 9h (referred to collectively as "9") located at strategic locations in the present biomaterial injection system 1. In the illustrated embodiment, sensor 9a is located between the reservoir 3 and the chamber 5. Sensor 9b is located between the chamber 5 and the purge device 7a. Another sensor 9c is located downstream of the purge device 7a. Sensor 9d is located close to the mold 13. In the preferred embodiment, the sensor 9d is located as close to the mold 13 as possible. The pressure sensor 9g is located substantially in the mold 13. The sensor 9h is optionally located in the intervertebral disc space 19, but outside the mold 13. The sensor 9e is located in the reservoir 3 and the sensor 9f is located in the actuator 21.

Figure 11:
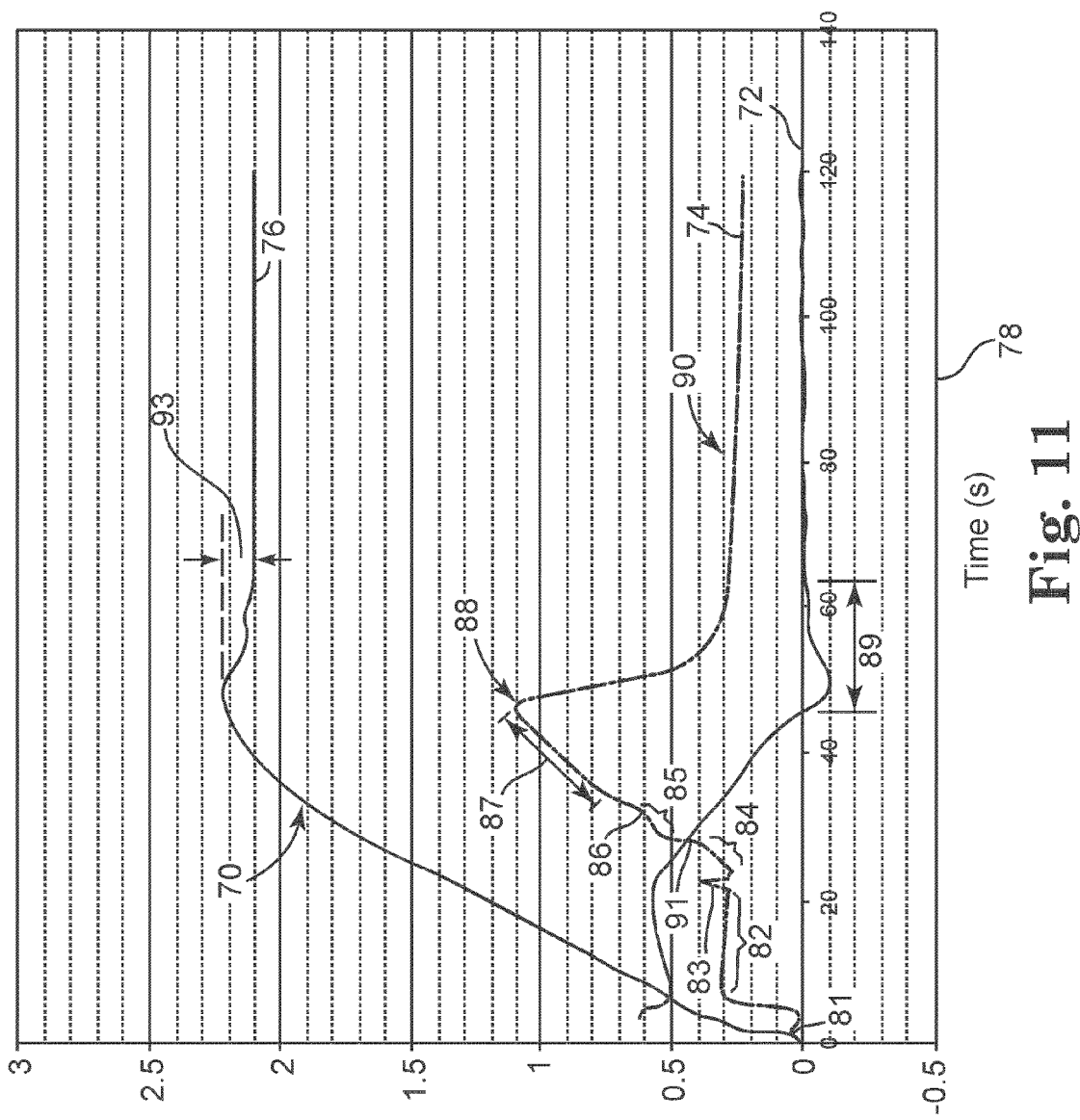
FIG. 11 is an exemplary injection profile in accordance with the present invention.

Each of the individual sensors 9 can measure any one of a plurality of injection conditions, such as for example biomaterial color, biomaterial viscosity, pressure, quantity and/or size of air bubbles in the biomaterial, flow rate, temperature, total volume, duration of the flow of the biomaterial 23, or any other injection condition that characterizes a proper injection profile. As used herein, "injection condition" refers to one or more dependent variables that are effected by one or more operating parameters. An "injection profile" refers to values of one or more injection conditions evaluated over time. An exemplary injection profile is illustrated in FIG. 11.

Output from the sensors 9 is preferably delivered to controller 15. The controller 15 preferably attaches a time/date stamp to all injection condition data. Not all of the sensors 9 necessarily perform the same function. For example, the sensors 9a and 9d may monitor pressure, while the sensor 9b monitors temperature and the sensor 9c monitors flow.

The sensors 9 can be in-line with the delivery tube 11, fluidly coupled to the delivery tube 11, coupled to the delivery tube 11 by a diaphragm, or engaged with the delivery tube using a variety of other techniques. The sensors 9 may be disposable or reusable. A suitable pressure sensor 9 can include any device or system adapted to measure or indicate fluid pressure within a surgical fluid system and adapted for attachment to a delivery mechanism 11. Examples of suitable pressure sensors include, but are not limited to, those involving a suitable combination of pressure gauge, electronic pressure transducer and/or force transducer components. Such components that can be adapted to permit the accurate and substantially real time measurement of pressure in a remote fluid, by shunting a sample of such fluid, can also be used particularly where the fluid is itself undergoing a change in properties in the course of its ongoing cure.

The various components of the biomaterial injection system 1 are preferably fabricated from polymeric or other materials that provide an optimal combination of properties such as compatibility with the biomaterial 23 and the ability to be sterilized and/or to be disposable.

Operation of the actuator 21 is preferably monitored and/or directed by the controller 15. Output from the sensors 9 is preferably delivered to the controller 15 to create a closed-loop feed back system. The controller 15 preferably includes a processor and a memory device. The controller 15 can be a special purpose computer, a general purpose computer such as a personal computer, independent signal conditioning circuits, threshold comparator circuits and switch circuits. In some embodiments, the controller 15 is a user interface to effect manual control of the system 1.

The controller 15 preferably includes one or more displays 16 that communicate injection conditions to the surgical staff. The controller 15 can also provide audio indications of the injection condition data shown on the displays 16. In another embodiment, the surgical staff manually overrides the operation of the controller 15 so as to permit one or more operating parameters to be controlled manually based on data obtained from the displays 16.

Figure 2:
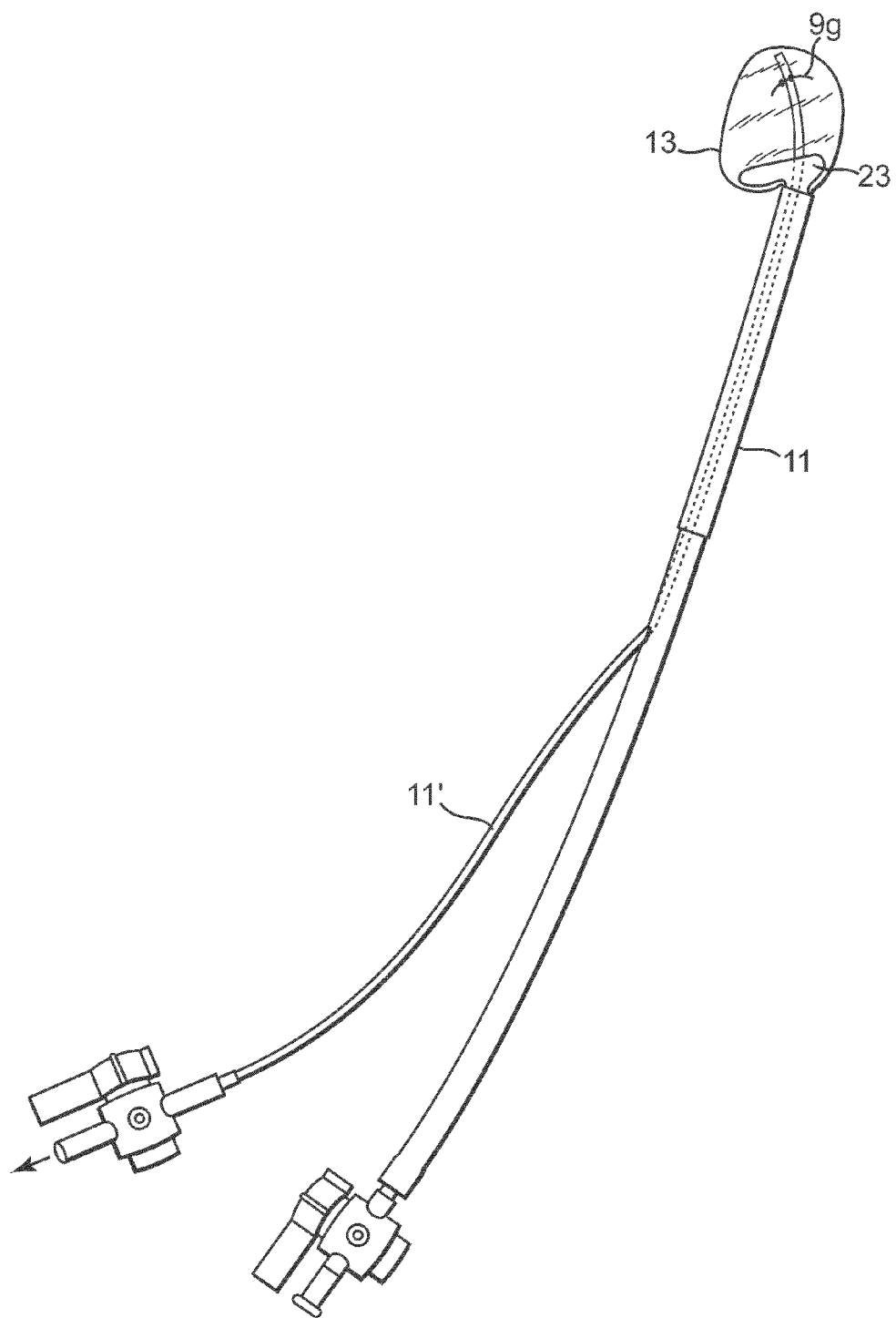
FIG. 2 is an exemplary delivery tube and mold in accordance with the present invention.

As illustrated in FIG. 2, the biomaterial injection system 1 also preferably includes a secondary tube 11' that evacuates air from the mold 13 before the biomaterial is delivered. The secondary tube 11' can either be inside or outside the delivery tube 11'. Removal of air from the mold 13 through the secondary tube 11' is preferably controlled by the controller 15. Connection to the sensor 9g in the mold 13 can optionally be connected through the secondary tube 11'.

Figure 3:
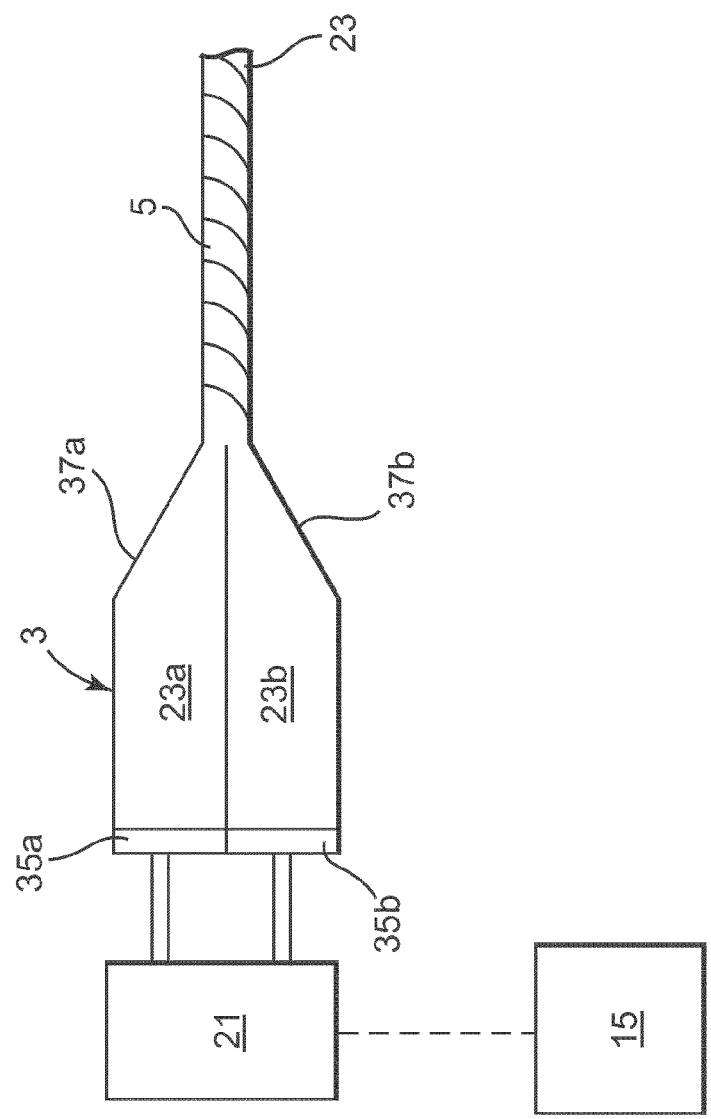
FIG. 3 is a schematic illustration of one embodiment of a biomaterial reservoir in accordance with the present invention.

FIG. 3 illustrates an embodiment where the reservoir 3 includes two or more discrete compartments 37a and 37b. Each compartment 37a, 37b is engaged with a piston 35a, 35b coupled to an actuator 21. As the actuator 21 advances the pistons 35a, 35b into the compartments 37a, 37b, respectively, components 23a, 23b of the biomaterial 23 flow into the chamber 5 where they are mixed.

The mixing of the two or more components 23a, 23b of the biomaterial 23 can initiate a chemical curing reaction. Although the reservoir of FIG. 3 is illustrated with two compartments 37a, 37b, three or more compartments can be used for applications where the biomaterial has more than two components.

Alternatively, the biomaterial may be a single component system that can be located in one or more of the compartments 37a, 37b. Single component biomaterials can be cured using, for example, ultraviolet light, ultrasonic energy, or heat. In one embodiment, the chamber 5 can optionally include an ultraviolet light source, a heater, or any other device or source of energy that initiates the curing process of the biomaterial 23.

Figure 4:
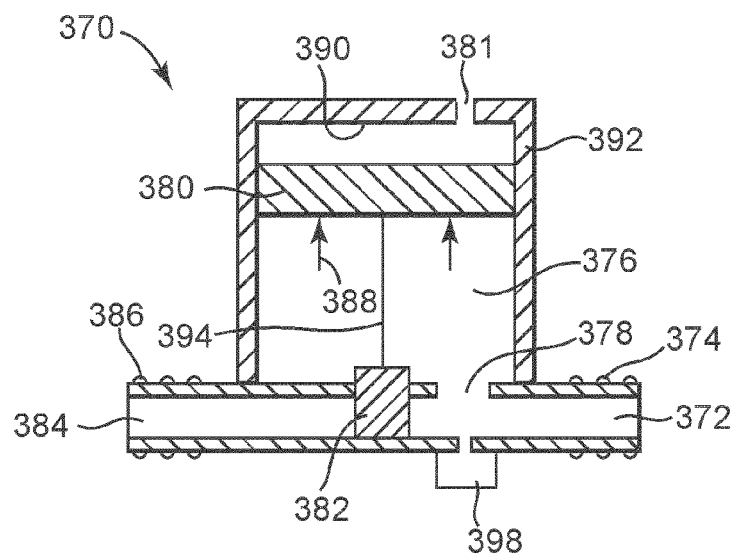
FIG. 4 is a schematic illustration of a purge device in accordance with the present invention.

FIG. 4 is a schematic illustration of an exemplary automatic purge device 370 in accordance with the present invention. The purge device 370 can optionally be substituted for the purge device 7a. Delivery tube 11 is fluidly coupled to inlet 372 using connecting structure 374. In the illustrated embodiment, connecting structure 374 is a plurality of threads. In an alternate embodiment, the connecting structure 374 can be a quick-connect device, or variety of other structures. The inlet 372 on the purge device 370 is fluidly coupled to chamber 376 by passageway 378. Piston 380 is located in the chamber 376. The purge device 370 is in a closed configuration with valve 382 obstructing the flow of biomaterial 23 to outlet 384. Outlet 384 also includes a connecting structure 386, such as threads.

As biomaterial is delivered to the inlet 372 under pressure, it is advanced through the passageway 378 into the chamber 376. The volume of the chamber 376 is designed to accommodate the optimum amount of biomaterial 23 that is typically purged prior to delivery to the mold 13. Once the chamber 376 is filled with biomaterial 23, force 388 is applied to the piston 380. As the piston 380 is driven toward surface 390 on housing 392 by the pressure of the biomaterial 23, connecting member 394 displaces the valve 382 along with the piston 380. Vent hole 381 allows air to escape from behind the piston 80 as it advances in the housing 392.

Figure 5:
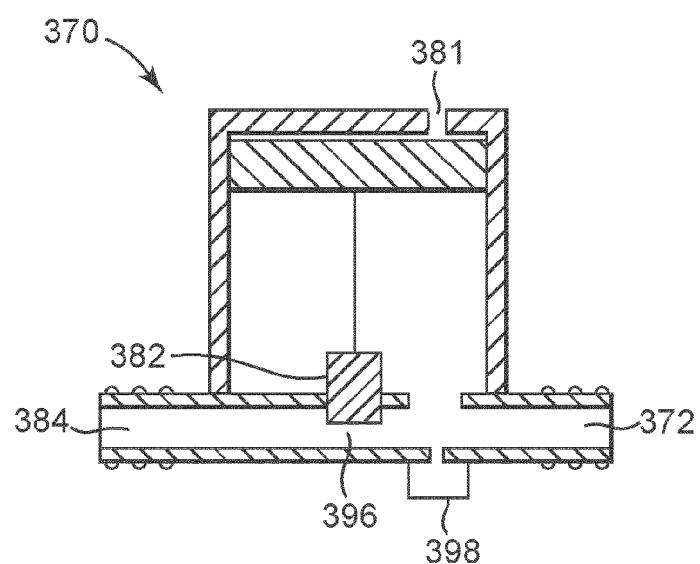
FIG. 5 illustrates the purge device of FIG. 4 in an open configuration.

FIG. 5 illustrates the purge device 370 of FIG. 4 in an open configuration. The piston 380 has been advanced all the way to the surface 390, causing the valve 382 to create an opening 396 through which the biomaterial 23 can be advanced to the outlet 384. Pressure transducer 398 is optionally located on the inlet side 372 of the valve 382 to measure the pressure of the bio-material 23 both before, during and after the valve 382 is opened.

FIG. 6A illustrates the biomaterial injection system 1 of FIG. 1, except that the annulus 25 acts as the mold to retain the biomaterial. As the biomaterial 23 is delivered to the annulus 25 it substantially fills the cavity 24. In one embodiment, the interior surface of the cavity 24 in the annulus 25 is coated with a reinforcing material 27, such as a curable polymer, prior to the delivery of the biomaterial. The reinforcing material 27 preferably adheres to the interior surface of the cavity 24. The reinforcing material 27 can be flexible and can be either permanent or bio-absorbable. In one embodiment, the reinforcing material 27 also adheres to the biomaterial, securing the biomaterial forming the implant to the inner surface of the cavity 24.

Figure 6C:
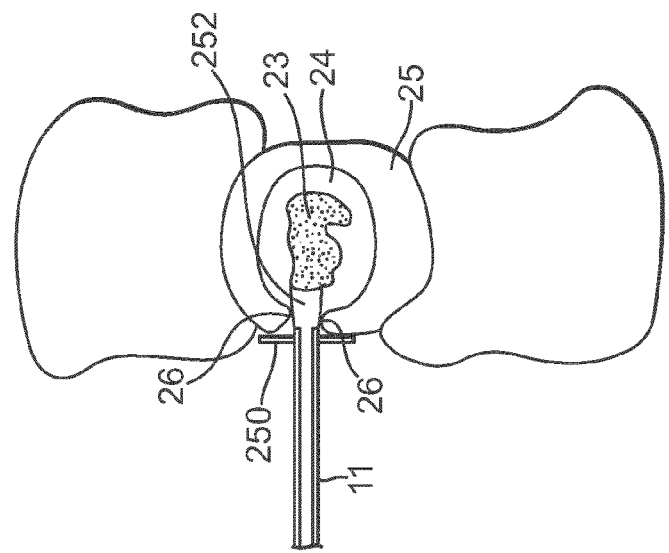
FIG. 6C is schematic illustration of the delivery tube of FIG. 6B sealed against the annulus.
Figure 6B:
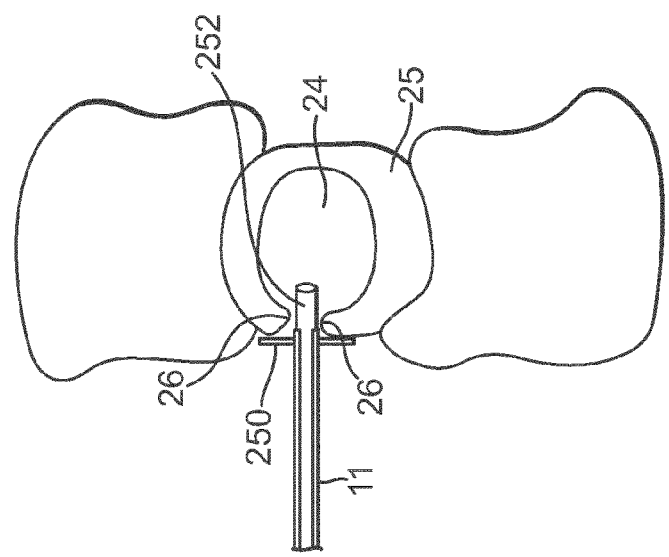
FIG. 6B is schematic illustration of a delivery tube that seals against the annulus in accordance with the present invention.

In another embodiment, the delivery tube 11 is sized to fit the inlet 26 formed in the annulus 25 snuggly to allow the biomaterial 23 to be delivered under pressure without leaking. In the embodiment of FIGS. 6B and 6C, flange 250 is located near distal end 252 of the delivery tube 11 to reduce or eliminate leakage of the biomaterial 23 from the cavity 24. Also illustrated in FIGS. 6B and 6C, distal end 252 of the delivery tube 11 adjacent to the inlet 26 includes a thin wall that expands when subjected to the pressure of the biomaterial 23 (see FIG. 6C). The expanded distal end 252 of the delivery tube 11 forms a seal with the inlet 26. The flange 250 and the thin-walled distal end 252 can either be used alone or in combination with each other.

Figure 7:
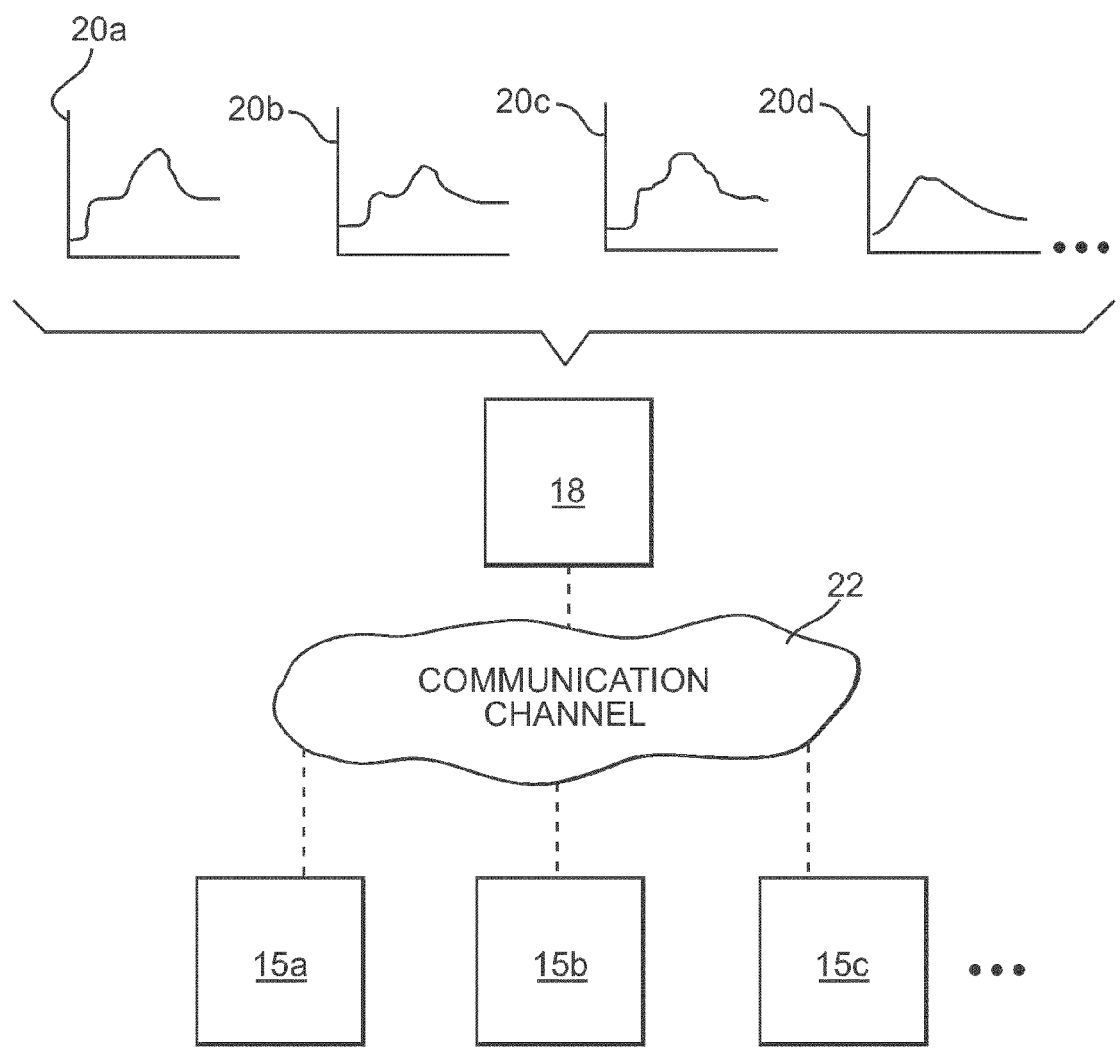
FIG. 7 is a schematic illustration of a communication system between a central computer and a plurality of controllers in accordance with the present invention.

As discussed above, the controller 15 preferably monitors and records the injection condition data and attaches a time/date stamp. FIG. 7 illustrates an embodiment in which a plurality of controllers 15a, 15b, 15c, ... (referred to collectively as "15") communicate with a remote computer 18 using a variety of communications channel 22, such as for example the Internet, phone lines, direct cable connection, wireless communication, and the like. The injection profiles 20a, 20b, 20c, 20d ... (referred to collectively as "20") for a plurality of patients are optionally uploaded to the computer 18 for storage and processing. Pre-surgical and post-surgical data about each patient is also preferably uploaded to the computer 18. Patient parameters typically includes weight, age, disc height after the procedure, disc degree index, disc compliance, and the like.

By linking the historic injection profiles 20 with the patient's pre-surgical and post-surgical patient parameters, a database is created that can be searched by surgeons for the injection profile 20 that most closely matches the current patient's parameters. Once the optimum profile is selected, it can optionally be downloaded to the controller 15 prior to performing the present method.

Preliminary Analysis of the Patient

The optimum injection profile and the corresponding injection conditions may vary as a function of patient parameters, such as for example, the patient's weight, age, gender, disc height, disc degeneration index, disc compliance, general clinical goals, patient-specific clinical goals, and the like. For example, a diseased disc may require a higher injection pressure and a higher termination pressure to restore more disc height and a longer dwell time at the threshold and/or termination pressure. Alternatively, if a bone scan indicates reduced bone density or that the vertebral bodies are otherwise compromised, a lower injection pressure may be indicated. The present invention includes creating an injection profile as a function of patient parameters and clinical goals. In some embodiments, a custom injection profile is created for each patient.

One mechanism for selecting the appropriate injection profile for the patient is to conduct an analysis on the annulus 25. Imaging or palpitation of the annulus, preferably after nuclectomy, is optionally performed before the delivery of the biomaterial to assess annular integrity. In one embodiment, an instrument is used that applies a known force to the annular wall 25 and measures the amount of deflection. In one embodiment, an evaluation mold 13' (which may be the same mold or a different mold than the implant mold 13), is inserted into the patient's annulus 25 after the nuclectomy is completed, such as illustrated in FIG. 1. The evaluation mold 13' is inflated with a contrast medium that is easily imaged or other liquid, such as saline, to a target pressure (see e.g., FIGS. 4-6). Inflation and deflation of the imaging mold 13' is preferably controlled by the present biomaterial injection system 1, and annular deflection is measured either automatically or manually. Alternatively, operations related to the evaluation mold 13' can be handled manually.

In some embodiments, the evaluation mold 13' and/or the delivery tube 11 have radiopaque properties. The radiopaque properties can be provided by constructing the evaluation mold 13' and/or the delivery tube 11 from a radiopaque material or including radiopaque markings, such as inks, particles, beads, and the like on the evaluation mold 13' and/or the delivery tube 11 to facilitate imaging. An image, such as an x-ray, MRI, CAT-scan, or ultrasound, is then taken of the patient's intervertebral disc space 19 to check if the nuclectomy (i.e., the cavity 24) is symmetrical, of adequate size, of the desired geometry and/or if the required amount of distraction has been achieved. This information is used by the surgeon to decide when the proper amount of nucleus material has been removed from the annulus 25.

The volume of contrast medium necessary to fill the cavity 24 and to achieve the desired amount of distraction, as verified by the image sequence, provides an indication of the volume of biomaterial 23 necessary for the procedure. In another embodiment, imaging is used to estimate the amount of nucleus that needs to be removed. The volume of liquid necessary to fill the evaluation mold 13' is then compared to the estimated volume measured using imaging techniques and a determination is made whether additional nucleus material should be removed.

Figure 8A:
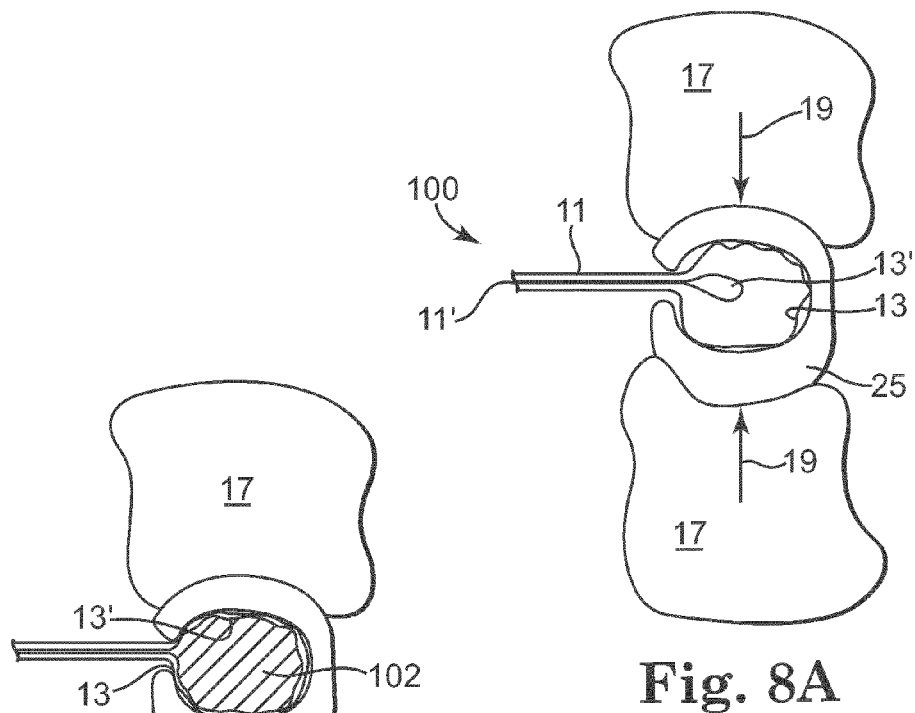
FIGS. 8A-8C illustrate an imaging and mold positioning technique in accordance with the present invention.
Figure 8B:
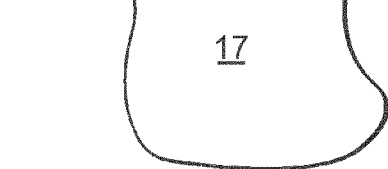
Figure 8C:
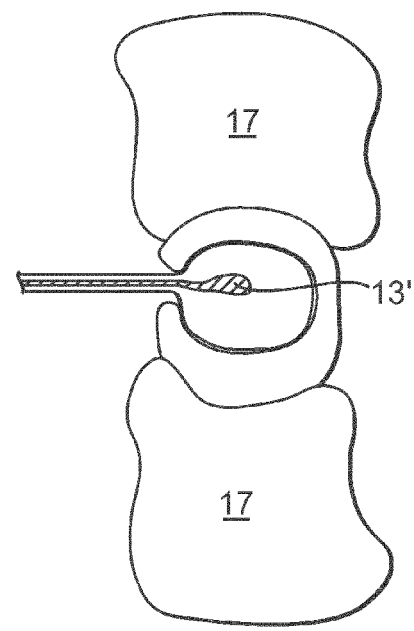

In another embodiment illustrated in FIGS. 8A-8C, an imaging device 100 including an evaluation mold 13' is positioned in the mold 13. After the mold 13 is positioned in the cavity 24 of the cavity 24 of the annulus 25 between the vertebrae 17, delivery tube 11' containing an evaluation mold 13' is inserted into the delivery tube 11. The evaluation mold 13' is preferably a small pliable, stretchable contrast balloon. A contrast medium 102 (see FIG. 10B) is delivered through the tube 11' into the evaluation mold 13' to fill the nominal volume of the mold 13. The mold 13 and/or the delivery tube 11 may also have radiopaque properties.

The contrast medium 102 is preferably delivered at a pressure sufficient to fully expand the mold 13 into the cavity 24. The evaluation mold 13' also serves to position the mold 13 within the annulus 25. As best illustrated in FIG. 8B, the fully expanded evaluation mold 13' corresponds generally to the shape of the cavity 24 within the annulus 25 that will be filled by the implant. Imaging, as discussed above, is then performed to confirm the shape of the cavity within the annulus 25 and placement of the mold 13 within the annulus 25. The quantity of contrast medium 102 can be used to estimate the volume of the cavity 24 within the annulus 25.

As illustrated in FIG. 8C, the contrast medium 102 is then removed from the evaluation mold 13'. The tube 11' and evaluation mold 13' are then removed from the delivery tube 11 in preparation for delivery of biomaterial 23 into the mold 13. The procedure of FIGS. 8A-8C can also be performed in connection with the embodiment of FIG. 6A, where the evaluation mold 13' is positioned directly in the cavity 24, rather than in the mold 13.

Figure 9:
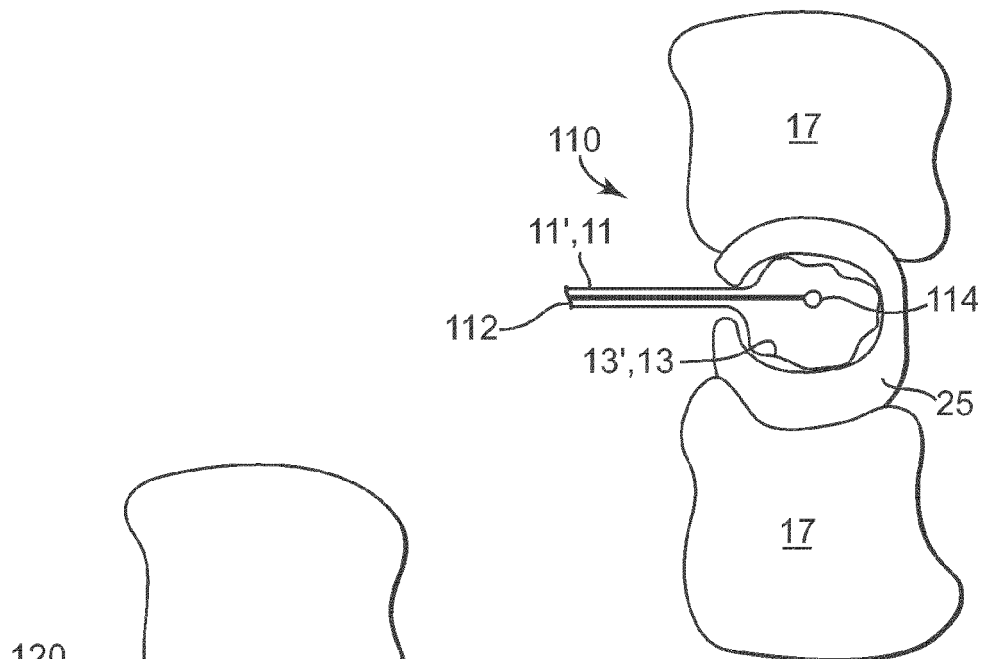
FIG. 9 illustrates an alternate imaging technique in accordance with the present invention.

FIG. 9 illustrates an alternate imaging method using imaging device 110 in accordance with the present invention. A guide wire or wire stylus 112 with an optional imaging target 114 at a distal end 116 is inserted into the delivery tube 11. The imaging target 114 can be a variety of shapes, preferably easily recognizable geometric shapes such as for example a sphere. Imaging techniques are then used to confirm the positioning of the evaluation mold 13' or the mold 13 in the annulus 25. The guide wire 112 can also be used to evaluate the geometry of the intervertebral disc space created by removal of nucleus material and/or to press the mold 13 into position within the annulus 25.

Figure 10A:
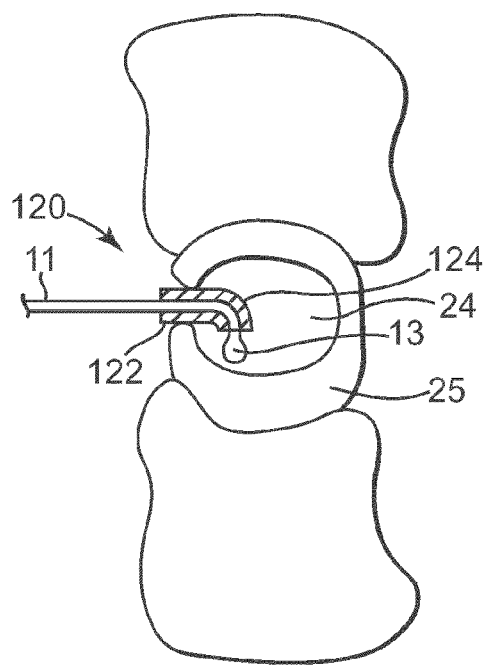
FIG. 10A-10B illustrate an alternate imaging technique using a radiopaque sheath in accordance with the present invention.
Figure 10B:
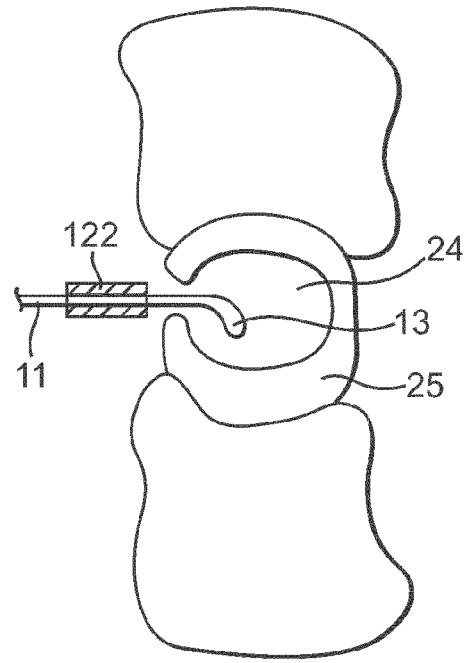

FIGS. 10A and 10B illustrate an alternate imaging technique using imaging device 120 in accordance with the present invention. The delivery tube 11 and mold 13 are provided with a radiopaque sheath 122. The delivery tube 11 and/or the mold 13 may also have radiopaque properties. In the illustrated embodiment, the radiopaque sheath 122 includes bend 124 that directs the mold 113 at a predetermined angle relative to the longitudinal axis of the delivery tube 11. Once positioned in the cavity 24 formed in the annulus 25, imaging techniques can be used to determine placement of the assembly in the cavity. Once positioning has been confirmed, the radiopaque sheath 122 can be withdrawn along the delivery tube 11 in preparation for delivery of biomaterial to the mold 13.

Compliance Testing

The evaluation mold 13' can also be used to measure the compliance of the annulus 25. For example, the evaluation mold 13' can be pressurized with a fixed volume of saline or a liquid contrast medium to the level anticipated during delivery of the biomaterial. Images of the intervertebral disc space 19 are optionally taken at various pressures to measure the distraction of the adjacent vertebrae 17. After a period of time, such as about three to about five minutes, the tissue surrounding the intervertebral disc space 19 generally relaxes, causing the pressure measured in the evaluation mold 13' to drop. Additional saline or contrast medium is then introduced into the evaluation mold 13' to increase the pressure in the intervertebral disc space 19 to the prior level. The tissue surrounding the intervertebral disc space 19 again relaxes as measured by the reduction in pressure within the evaluation mold 13'. By repeating this procedure several times, the surgeon can assess the compliance of the intervertebral disc space 19 and/or the annulus 25, and the likely volume of biomaterial 23 necessary for the procedure.

In another embodiment, compliance is measured by continuously adding a liquid to the evaluation mold 13' at a rate sufficient to maintain a generally constant pressure in the biomaterial delivery system 1 and/or in the intervertebral disc space. The change in the rate at which liquid needs to be added to maintain a constant pressure provides information that can be used to estimate compliance of the annulus 25 and/or the intervertebral disc space 19.

A healthy, compliant annulus can typically handle several pressurization/relaxation cycles. A diseased annulus 25 may show less relaxation (e.g., less compliance) after being pressurized. Depending upon the status of the annulus 25 and the intervertebral disc space 19, a patient-appropriate injection profile can be selected.

This compliance evaluation can be either controlled manually or by the controller 15. The compliance data collected can be used to determine the operating parameters to produce the injection profile best suited to the patient.

Injection Conditions

The present biomaterial delivery system 1 permits one or more operating parameters to be controlled to achieve the desired injection conditions. The injection conditions are monitored, recorded and controlled real-time. The injection conditions may include, for example, biomaterial temperature and viscosity, biomaterial flow rate, biomaterial pressure, volume of biomaterial, distraction pressure, total distraction, and time, such as for example distraction time. These injection conditions can vary over the course of the medical procedure, so a plurality of injection conditions are preferably monitored and recorded as a function of time. The injection conditions can also be evaluated as a function of any of the other injection conditions, such as for example, pressure as a function of volume or flow. In the present invention, the pressure in the mold 13 is one possible injection condition for determining when to terminate the flow of biomaterial 23. Alternatively, the volume of biomaterial 23 delivered to the mold 13 can also be used for this purpose.

Once an optimum injection profile for the patient is determined (see e.g., FIG. 11), the controller 15 preferably controls one or more operating parameters so that the injection conditions are maintained within a predetermined margin of error.

The injection conditions can be used to signal that the procedure is 10 out of specification. Alternatively, the controller 15 can calculate trends or slopes of the injection conditions to predict whether a particular injection condition will likely be out of specification. As used herein, "out of specification" refers to one or more injection conditions that have deviated from the desired injection profile and/or are exhibiting a trend that indicates a future deviation from the injection profile.

In those situations where the injection conditions can not be brought under control, such as for example if the mold 13 malfunctions, the procedure is aborted and the biomaterial 23 is preferably withdrawn from the patient before it cures. As used herein, malfunction refers to ruptures, fractures, punctures, deformities, kinks, bends, or any other defect that results in more or less biomaterial being injected into the patient than would otherwise occur if the mold was operating as intended. Alternatively, if the malfunction occurs in a location other than the mold, such as in the delivery tube 11 or if the mold kinks and can not be deployed and expanded to fill the intervertebral disc space, or if the vacuum tube 11' is obstructed an air in the mold 13 can not be evacuated, less biomaterial will be injected into the mold than is desired.

The controller 15 monitors one or more sensors 9 to determine if the injection conditions are under control. If any one or a combination of the injection conditions are out of specification, a number of corrective actions can be taken. If the deviation from the preferred injection profile is minor, the controller 15 can attempt a correction. During a given medical procedure where the resistance to the flow of biomaterial 23 is essentially fixed, the primary mechanisms for controlling the injection conditions are 1) decreasing, increasing or reversing the drive pressure exerted on the reservoir 3 by the actuator 21; 2) releasing biomaterial 23 through one or more of the purge devices 7a, 7b; and 3) changing the temperature, and hence the viscosity, of the biomaterial 23.

If the deviation is above a particular threshold, the controller 15 may signal the surgical staff. Alternatively, the surgical staff can monitor the displays 16 for any out of specification injection conditions. The displays 16 preferably highlight the injection condition(s) that have deviated from the preferred injection profile. In those instances where an injection condition is seriously out of specification, the controller 15 will signal that the procedure should be aborted and/or automatically abort the procedure. Typically, the actuator 21 will decrease or reverse the drive pressure on the reservoir 3 in anticipation of aborting the procedure. If the procedure is aborted, any biomaterial 23 in the mold 13 and/or the intervertebral space 19 is removed, either through the purge device 7b or manually by the surgeon. The mold 13 is also removed.

FIG. 11 illustrates a simulated injection profile 70 that illustrates the benefits of the present biomaterial delivery system 1. The injection profile 70 includes three injection condition curves for flow rate 72, injection pressure 74 and total volume 76 all as a function of time 78. In the illustrated example, the flow 72 is calculated by the controller 15, the injection pressure 74 is measured as the sensor 9b and/or 9c, and the volume 76 is measured by the sensor 9f. In another embodiment, the injection profile may include flow, pressure or volume curves measured at other locations along the biomaterial injection system 1.

At the beginning of time sequence 81, the biomaterial 23 is immediately upstream of the purge device 7a. During time sequence 81, the biomaterial 23 begins to enter the purge device 7a. During time sequence 82, the biomaterial 23 is filling the purge device. The flow rate 72 is relatively constant and the total volume 76 of biomaterial continues to increase. The sudden increase of injection pressure 74 between the end of time sequence 81 and the beginning of time sequence 82 is the result of internal resistance to the flow of biomaterial 23 at the purge device 7a.

At time sequence 83, the purge device 7a switches the flow of biomaterial 23 to the delivery tube 11, resulting in a rapid spike in injection pressure 74. At time sequence 84, the biomaterial 23 fills the delivery tube 11. Injection pressure 74 increases due to resistance to the flow of biomaterial 23 through the delivery tube 11. At time sequence 91, the biomaterial 23 reaches the folded mold 13, resulting in a rapid increase in injection pressure 74 as the mold unfolds.

At time sequence 85 the biomaterial 23 begins to fill the mold 13. The slight drop in injection pressure 74 is the result of the biomaterial 23 flowing freely into the mold 13. The expanding mold 13 hits the inner wall of the annulus at time sequence 86. The flow rate 72 continues to drop and the total volume 76 of biomaterial 23 continues to increase at a generally constant rate. At time sequence 87, the injection pressure 74 of the biomaterial 23 continues to increase at a different rate as it displaces the vertebrae 17 and distracts the intervertebral disc space 19. The muscles and tendons attached to the vertebrate 17 are stretched elastically by the injection pressure 74 of the biomaterial 23 in the mold 13.

At time sequence 88, the threshold injection pressure 74 is reached. Time sequence 88 represents the maximum distraction of the intervertebral disc space 19. In the illustrated example, the drive pressure exerted by the actuator 21 on the reservoir 3 during time sequences 81 through 88 is generally constant. Once the injection pressure 74 at time sequence 88 is reached, a transition is triggered where the drive pressure at the actuator 21 is reduced from a first operating parameter to a second operating parameter. As a result, the injection pressure 74 is reduced. The flow rate 72 is about zero and the total volume 76 of biomaterial is at a maximum.

In another embodiment, once the injection pressure 74 at time sequence 88 is reached, a transition is triggered from a first operating parameter to a second operating parameter where the drive pressure at the actuator 21 is held constant for some period of time, such as for example 3-120 seconds. At the end of the dwell time, the drive pressure is reduced from the second operating parameter to a third operating parameter. Again, the injection pressure 74 is reduced and the flow rate 72 is about zero and the total volume 76 of biomaterial is at its final volume.

At time sequence 89 the drive pressure exerted on the biomaterial 23 in the reservoir 3 by the actuator 21 is reduced. This reduction can alternatively be achieved by releasing a portion of the biomaterial 23 through a purge device 7a, 7b. The pressure created in the intervertebral disc space 19 acting on the mold 3 is now greater than the injection pressure 74 of the biomaterial 23 in the biomaterial delivery system 1. Consequently, tension of the muscles and tendons surrounding the vertebrate 17 provides a compressive force that results in a flow of biomaterial 23 out of the mold 13, as indicated by the negative flow rate 72 during time sequence 89 and a decrease in total volume 93.

At time sequence 90 the injection pressure 74 of the biomaterial 23 is generally constant. The pressure exerted by the mold 13 and biomaterial 23 is nearly in balance with the pressure exerted by the vertebrate 17 on the mold 13. The flow rate 72 and the change in total volume 76 are both about zero. With the system 1 now in stasis, the biomaterial 23 begins to cure. Once the biomaterial 23 is at least partially cured, the delivery tube 11 is removed.

Figure 12:
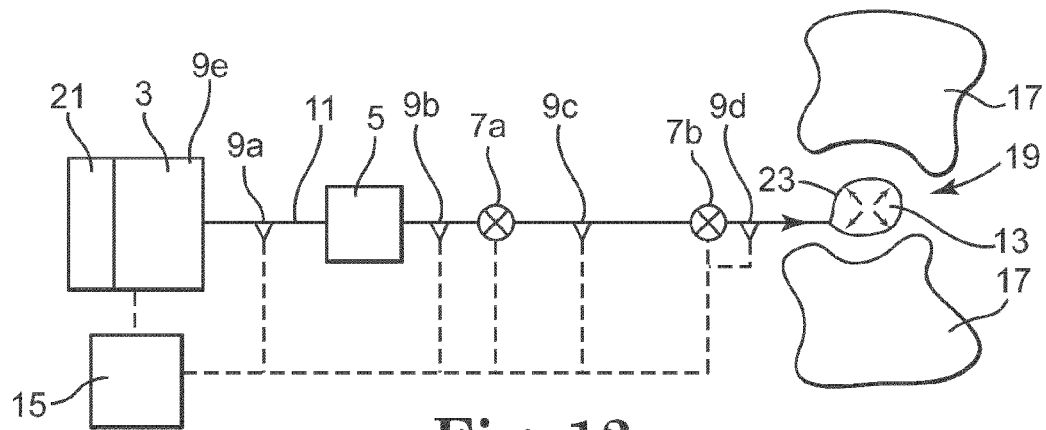
FIGS. 12-14 are schematic illustrations of one method in accordance with the present invention.
Figure 13:
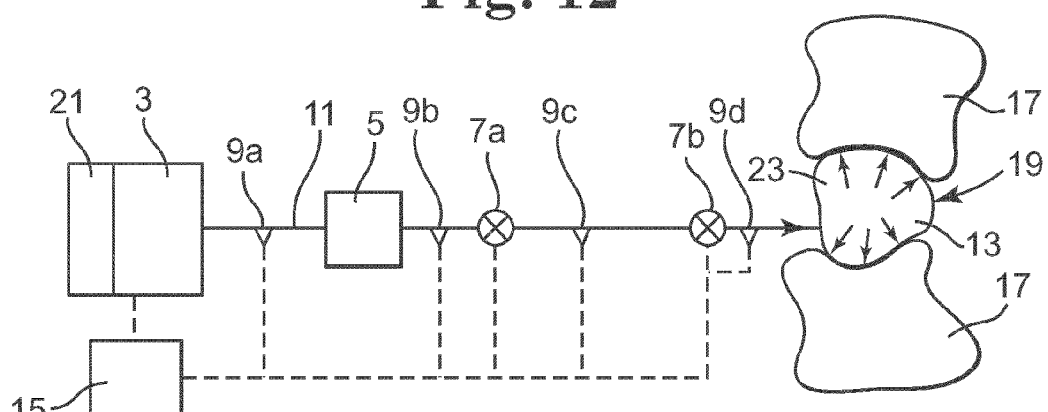
Figure 14:
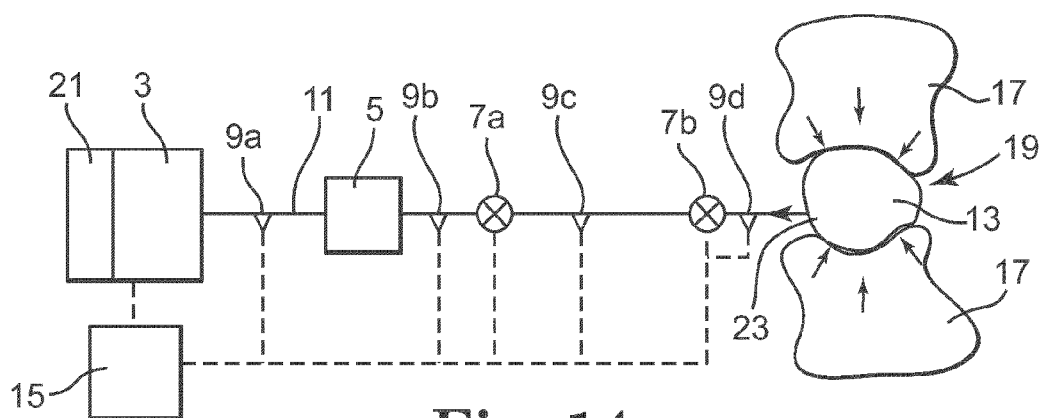

FIGS. 12-14 schematically illustrate one embodiment of the present invention. The embodiments of FIGS. 12-14 are illustrated as a complete disc replacement. The embodiments of these Figures are equally applicable to a full or partial nucleus replacement.

In these embodiment, the biomaterial injection system 1 initially operates at a first operating parameter. When one of the injection conditions reaches a threshold level, such as for example a threshold pressure as measured in the mold 13, the controller 15 switches or transitions to second operating parameter. In an alternate embodiment, the threshold trigger could be flow rate, time, volume or temperature of the biomaterial. In the embodiment of FIGS. 12-14, the trigger from the first to the second operating parameter causes the controller to reduce the pressure applied by the actuator 21 on the biomaterial 23 in the reservoir 3.

In another embodiment, the second operating parameter is a dwell cycle where the pressure is maintained as some predetermined level for a predetermined period of time. At the end of the dwell cycle, the controller switches to a third operating parameter, which includes reducing the pressure applied by the actuator 21 on the biomaterial 23 in the reservoir 3.

FIG. 12 illustrates a first operating parameter during which the deflated mold 13 is filled with biomaterial 23 until it conforms to the shape of the intervertebral disc space 19. In one embodiment the first operating parameter includes a drive pressure created by the actuator 21 which results in an injection parameter (i.e., injection pressure) measured at the sensor 9e of about 150 psi. Alternatively, the first operating parameter includes a drive pressure created by the actuator that results in an injection pressure in the range of about 100 psi to about 270 psi.

The relatively high injection pressure provides a number of benefits, including rapid filling of the mold 13 to reduce the chance of leaving voids or under-filled regions. The biomaterial injection system 1 continues to operate at the first operating parameter until one of the injection conditions reaches a threshold level that triggers use of the second operating parameter.

FIG. 13 depicts the time sequence in the procedure when the pressure of the biomaterial 23 measured at the sensors 9b, 9c, and preferably the sensor 9d, triggers the controller 15 to change to second operating parameter. Once the injection pressure measured at the sensors 9b, 9c or 9d rises to a particular level, the drive pressure exerted by the actuator 21 is reduced to a predetermined level.

The injection pressure used to determine a suitable threshold typically corresponds to the distraction pressure brought about by the delivery of biomaterial 23 within the disc space 19. The injection condition in this instance is the injection pressure measured at the sensors 9c or 9d, such as for example about 80 psi to about 150 psi. In one embodiment, the injection pressure triggers the controller 15 to transition to the second operation condition. In another embodiment, the second operating condition holds the injection pressure at a predetermined level for a predetermined dwell time.

FIG. 14 illustrates the second operating parameter (or a third operating parameter where the second operating parameter is a dwell cycle). In the embodiment of FIG. 14, the second operating parameter includes a reduction in drive pressure exerted by the actuator 21. The tension built up in the tissues surrounding the vertebrate 17 is permitted to act on the mold 13 to expel a portion of the biomaterial 23 out of the intervertebral disc space 19 and back into the delivery tube 11. In one embodiment, the injection pressure measured at sensor 9a during the second operating parameter is about 0 psi to about 120 psi, and typically about 10 psi to about 50 psi.

It is possible to measure the pressures discussed above using any of the sensors 9a-9d and 9g-9h. Doing so would require calibrating the biomaterial injection system 1 so that a measured pressure at one of the sensors 9 is correlated to the actual pressure in the intervertebral disc space 19, such as measured by sensor 9g or 9h. The factors required for such a calibration include the size of the mold 13, the resistance to fluid flow between the reservoir 3 and the mold 13, the flow rate, the viscosity and temperature of the biomaterial 23, the cure time of the biomaterial, and a variety of other factors. For example, with regard to mold size, the transition from the first operating parameter to the second operating parameter occurs when the injection conditions measured at the sensor 9b is about 100 psi to about 125 psi for a mold 13 with a volume of about 1.8 cubic centimeters; about 105 psi to about 130 psi for a mold 13 with a volume of about 2.7 cubic centimeters; and about 110 psi to about 135 psi for a mold with a volume of about 4.0 cubic centimeters.

Figure 15:
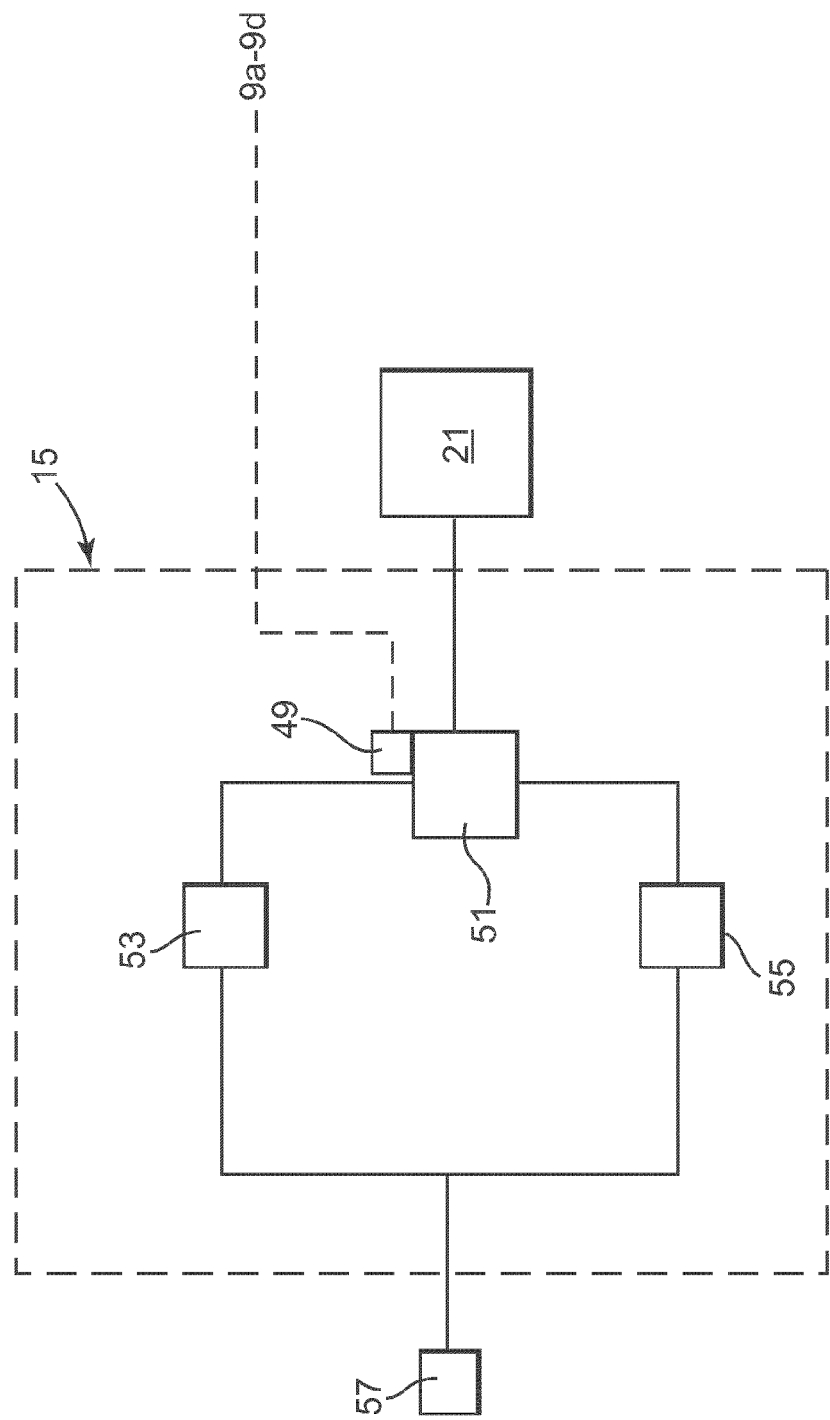
FIG. 15 illustrates an alternate embodiment of the present method and apparatus.

FIG. 15 illustrates an alternate method and apparatus for performing the present invention where the actuator 21 is attached to an external source of compressed air 57. The controller 15 includes a directional control valve 49 that extends or retracts the pneumatic actuator 21 and a pressure control switch 51 to change between the first operating parameter and the second operating parameter. At least two pressure regulators 53, 55 are used to regulate the pressure reaching the pressure control switch 51. The first pressure regulator 53 provides the first pressure injection and the second pressure regulator 55 provides the second pressure injection. In an embodiment where the operating parameters comprise multiple variables, multiple pressure regulators will typically be required.

Initially, the pneumatic actuator 21 is supplied with compressed air through the first pressure regulator 53. When one or more of the sensors 9a-9d detects a threshold pressure, the pressure control switch 51 selects compressed air from the second pressure regulator 55 to drive the pneumatic actuator 21. In one embodiment, the directional control valve 49 is a normally open, four-way valve such as those available under the trade name of Four-Way Valve (SV271) available from Omega Engineering, Inc. Stamford, Conn.

Mold Placement

In a related embodiment, the mold, or a kit that contains or is adapted for use with such a mold, can include tools adapted to position the mold 13 in situ. In one embodiment, the tool is a guide wire, such as for example the guide wire shown in FIG. 9, that is placed through the delivery conduit 11 itself, or preferably through an air passageway that terminates at or near the point of contact with the mold 13. The guide wire can be designed to substantially assume the curved contour of the extended but unfilled mold, and to provide a plane of orientation, in order to both facilitate placement of the mold and provide an outline of the periphery of the mold in position and prior to filling. Thereafter, the guide wire can be removed from the site prior to delivery of the biomaterial and air evacuation. The use of a guide wire in this manner is particularly facilitated by the use of an air passageway that is unconnected to, and positioned outside of, the biomaterial delivery tube. In another embodiment, the delivery tube 11 includes one or more curves that facilitate placement of the mold 13.

Optionally, and in order to facilitate the placement of the collapsed mold 13 within a sheath, the invention further provides a rod, e.g., a plastic core material or a metal wire, dimensioned to be placed within the mold 13, preferably by extending the rod through the conduit. Once in place, a vacuum can be drawn on the mold 13 through the air passageway in order to collapse the mold 13 around the rod. Simultaneously, the mold 13 can also be twisted or otherwise positioned into a desired conformation to facilitate a particular desired unfolding pattern when later inflated or filled with biomaterial. Provided the user has, or is provided with, a suitable vacuum source, the step of collapsing the mold 13 in this manner can be accomplished at any suitable time, including just prior to use.

In certain embodiments it will be desirable to collapse the mold 13 just prior to its use, e.g., when using mold materials that may tend to stick together or lose structural integrity over the course of extended storage in a collapsed form. Alternatively, such mold materials can be provided with a suitable surface coating, e.g., a covalently or noncovalently bound polymeric coating, in order to improve the lubricity of the surface and thereby minimize the chance that contacting mold surfaces will adhere to each other. In another embodiment, the outer surface of the mold 13 can be coated with a material that bonds to the inner surface of the cavity 24 in the annulus 25.

FIG. 16A illustrates the delivery tube 200 and mold 13 with a bend 202 at the connection 204 between the mold 13 and the delivery tube 11. In the illustrated embodiment, the bend 202 extends along about 3-5 millimeters of the delivery tube 200 near the connection 204 and has a curvature of about 30°+/−15°. As illustrated in FIG. 16B, this configuration is particularly well suited for posterior entry into the annulus 25. The embodiment of FIG. 16A can also be achieved with a straight, flexible delivery tube and a curved guide wire 206 in the delivery tube 200.

FIG. 17A illustrates a curved delivery tube 210. As illustrated in FIG. 17B, this configuration is particularly well suited for lateral entry of the mold 13 into the annulus 25. The curve of the delivery tube 210 can also be achieved by using a flexible delivery tube containing a curved guide wire. In another embodiment, the guide wire may be malleable.

FIG. 18 illustrates a delivery tube 220 with multiple bends 222, 224, 226. The bends 222, 224, 226 can be co-planar or located in multiple planes. The bend 226 is located near the connection 228 with the mold 13, similar to FIG. 16A. FIG. 19 illustrates the mold 13 attached to an alternate delivery tube 230 with bends 232, 234. Similarly, the bends 232, 234 can be co-planar or located in multiple planes. Alternatively, the embodiments of FIGS. 18 and 19 can be achieved by using a flexible delivery tube containing a curved guide wire.

Biomaterials

The method of the present invention can be used with any suitable curable biomaterial such as a curable polyurethane composition having a plurality of parts capable of being aseptically processed or sterilized, stably stored, and mixed at the time of use in order to provide a flowable composition and initiate cure, the parts including: (1) a quasi-prepolymer component comprising the reaction product of one or more polyols, and one or more diisocyanates, optionally, one or more hydrophobic additives, and (2) a curative component comprising one or more polyols, one or more chain extenders, one or more catalysts, and optionally, other ingredients such as an antioxidant, hydrophobic additive, dyes and radiopaque markers. Upon mixing, the biomaterial is sufficiently flowable to permit it to be delivered to the body and fully cured under physiological conditions. A suitable biomaterial also includes component parts that are themselves flowable at injection temperature, or can be rendered flowable, in order to facilitate their mixing and use. Additional discussion of suitable biomaterials can be found in U.S. patent application Ser. Nos. 10/365,868 and 10/365,842, previously incorporated by reference.

The biomaterial used in this invention can also include polyurethane prepolymer components that react in situ to form a solid polyurethane ("PU"). The formed PU, in turn, includes both hard and soft segments. The hard segments are typically comprised of stiffer oligourethane units formed from diisocyanate and chain extender, while the soft segments are typically comprised of more flexible polyol units. These two types of segments will generally phase separate to form hard and soft segment domains because these segments tend to be thermodynamically incompatible with one another.

Those skilled in the relevant art, given the present teaching, will appreciate the manner in which the relative amounts of the hard and soft segments in the formed polyurethane, as well as the degree of phase segregation, can have a significant impact on the final physical and mechanical properties of the polymer. Those skilled in the art will therefore further appreciate the manner in which such polymer compositions can be manipulated to produce cured and curing polymers with a desired combination of properties within the scope of this invention. In some embodiments of the present invention, for instance, the hard segment in the formed PU ranges from about 20% to about 50% by weight and more preferably from about 20% to about 30% by weight and the soft segment from about 50% to about 80% and more preferably from about 70% to about 80% by weight, based on the total composition of the formed PU. Other embodiments may be outside of these ranges.

The biomaterial typically includes a plurality of component parts and employs one or more catalysts. The component parts, including catalyst, can be mixed to initiate cure, and then delivered, set and fully cured under conditions such as time and exotherm sufficient for its desired purpose. Upon the completion of cure, the resultant biomaterial provides an optimal combination of properties for use in repairing or replacing injured or damaged tissue. In a further embodiment, the biomaterial provides an optimal combination of properties such as compatibility and stability, in situ cure capability and characteristics (e.g., extractable levels, biocompatibility, thermal/mechanical properties), mechanical properties (e.g., tensile, tear and fatigue properties), and biostability.

Many mixing devices and methods have been used for biomaterials having a plurality of parts such as bone cement and tissue sealant. Mechanical mixing devices, such as the ones disclosed in U.S. Pat. No. 5,797,679 (Grulke, et al.) and U.S. Pat. No. 6,042,262 (Hajianpour), have been used for bone cement mixing. These mechanical mixing devices, however, can take a long time to get thorough mixing and can be difficult to operate in sterile field, especially for biomaterials having a plurality of parts with short cure time. On the other hand, some prior art two-part polyurethanes have a gel time of about 30 minutes. Without a proper seal method to seal off the delivery tube, a cure time of 30 minutes can be too long for operating room use.

It is important that mixing of the biomaterial occurs quickly and completely in the operating room in a sterile fashion. Biomaterial with induction times of less than 60 seconds and cure times of less than 5 minutes require a different mixing and delivery device than biomaterials of about 15 minutes of cure time. For biomaterial having two-part issocyanate-based polyurethane biomaterials, due to the sensitivity of NCO to OH ratio to the final properties of the cured biomaterial, there are several features that are important to the final properties of the in situ cured biomaterial. Several factors appear to have an impact on the in situ curable biomaterial mixing and delivery such as the number of mixing elements, purging of the initial volume from the static mixer and the effect of polymer flow during delivery using a static mixer.

The compatibility of the biomaterial can also be achieved by having more than the traditional two parts, e.g., three or more parts, and mixing them all together prior to polymer application. By storing the incompatible components in different cartridges and/or preconditioning each component according to individual requirements, it often can minimize the concern of component incompatibility. One example of a three-part biomaterial is to separate the polyol and chain extender in a two-part biomaterial.

In situ curability is largely dependent on the reaction rate, which can be measured by induction time and cure time. In general, fast cure (short induction time) will improve in situ curability by providing more complete polymerization, less leachable components, and better mechanical properties (e.g., less "cold layer" formed due to the cold surface of the implant). However, induction time should also be balanced with adequate working time needed for biomaterial injection, distraction, to provide enough time to access the injection conditions, identify if the injection conditions fall inside or outside an acceptable range, and if falling outside the acceptable range, halting or reversing the injection process.

Particularly for use in the disc, it has been determined that shorter induction times tend to provide improved biomaterial properties. For such uses, the induction time can be between about 5 and about 60 seconds, for instance, between about 5 and about 30 seconds, and between about 5 and about 15 seconds. By comparison, the total cure time for such biomaterial can be on the order of 5 minutes or less, 3 minutes or less, and one minute or less. In one embodiment of the present invention, however, the cure time can be on the order of about 15 minutes. In either case the cure time can be greater than 15 minutes by adjusting the amount of catalyst used.

The method of the present invention can be used for a variety of applications, including for instance, to provide a balloon-like mold for use preparing a solid or intact prosthesis, e.g., for use in articulating joint repair or replacement and intervertebral disc repair. Alternatively, the method can be used to provide a hollow mold, such as a sleeve-like tubular mold for use in preparing implanted passageways, e.g., in the form of catheters, such as stents, shunts, or grafts.

The present invention also provides a method and system for the repair of natural tissue that involves the delivery of biomaterial using minimally invasive mechanism, the composition being curable in situ in order to provide a permanent replacement for natural tissue. Optionally, the biomaterial is delivered to a mold that is positioned by minimally invasive mechanism and filled with biomaterial composition, which is then cured in order to retain the mold and cured composition in situ.

As can be seen, the annular shell can itself serve as a suitable mold for the delivery and curing of biomaterial. Optionally, the interior surface of the annular shell can be treated or covered with a suitable material in order to enhance its integrity and use as a mold. One or more inflatable devices, such as the molds described herein, can be used to provide molds for the delivery of biomaterial. The same inflatable devices used to distract the joint space can further function as molds for the delivery and curing of biomaterial.

The method of the present invention can also be used to repair other joints, including diarthroidal and amphiarthroidal joints. Examples of suitable diarthroidal joints include the ginglymus (a hinge joint, as in the interphalangeal joints and the joint between the humerus and the ulna);

throchoides (a pivot joint, as in superior radio-ulnar articulation and atlanto-axial joint); condyloid (ovoid head with elliptical cavity, as in the wrist joint);

reciprocal reception (saddle joint formed of convex and concave surfaces, as in the carpo-metacarpal joint of the thumb); enarthrosis (ball and socket joint, as in the hip and shoulder joints) and arthrodia (gliding joint, as in the carpal and tarsal articulations).

Implant Procedure

An illustration of the surgical use of one embodiment of the intervertebral prosthesis system of the invention is as follows 1) A nuclectomy is performed by surgically accessing the nucleus through one or more annulotomies and removing at least a portion of the nucleus of the disc to form a cavity. The cavity is preferably symmetrical relative to the spine.

2) The distal (patient end) portion of a device of this invention is inserted into the surgical site and intervertebral space. In one embodiment, the distal tip contains a deflated mold. The mold is then inserted into the intervertebral disc space by pushing the distal end of the biomaterial delivery portion in a longitudinal direction through the annulotomy in the direction of the disc to the extent necessary to position the mold only into the nuclear cavity.

3) Optionally, if pre-distraction of the intervertebral disc is needed when the patient has pre-existing disc height loss, it can be accomplished using any suitable intervertebral distraction mechanism, including both external and internal mechanism. Internal distraction can be accomplished by using an apparatus similar to that of the invention, e.g., by first delivering a suitable solution (e.g., saline or contrast solution) into the mold in order to exert a force sufficient to "distract" the intervertebral joint to the desired extent. After the distraction, the solution can be removed from the mold by applying vacuum. It is optional either to use the same mold for hosting the injectable biomaterial or to replace the distraction mold with a new mold.

4) The components of a biomaterial delivery system are assembled as generally illustrated in FIG. 1a.

5) The controller applies a first pressure to the biomaterial in the reservoir. For embodiments that use multi-part biomaterials, the biomaterial components are forced by positive pressure out of the reservoir and through a static mixer. The initially inadequately mixed portion of the mixed biomaterial are preferably shunted through a purge device. Once the initial portion of the biomaterial has been shunted, the valve is redirected to permit the biomaterial to continue onward through the flow path and into the mold.

6) When the fluid pressure of the biomaterial in the biomaterial delivery system and/or the mold reaches a threshold operating parameter, such as the measured injection pressure, the controller reduces the pressure on the reservoir to a second pressure. The second pressure permits the tissues of the intervertebral disc space to expel a portion of the biomaterial out of the mold and back into the biomaterial injection system.

7) When the desired pressure has been reached, the parameters are maintained during the curing phase of the biomaterial.

8) The delivery tube is detached from the mold, thereby leaving the filled mold containing the cured biomaterial in situ to function as an intervertebral disc prosthesis.

9) The patient is sutured and closed and permitted to recover from the surgery.

Patents and patent applications disclosed herein, including those cited in the Background of the Invention, are hereby incorporated by reference. Other embodiments of the invention are possible. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of filling an intervertebral disc space with a flowable biomaterial, comprising the steps of:
    fluidly coupling a reservoir containing the flowable biomaterial to the intervertebral disc space;
    performing automatically in a controller the steps of;
        monitoring at least one sensor that measures at least one injection condition of the flowable biomaterial;
        controlling a flow of the flowable biomaterial into the intervertebral disc space in accordance with a first operating parameter, wherein pressure of the flowable biomaterial increases rapidly during at least a portion of the delivery into the intervertebral disc space;
        receiving a signal from the sensor that the at least one injection condition has reached a threshold level corresponding to the biomaterial substantially filling the intervertebral space;
        reducing the flow of the flowable material into the intervertebral disc space in response to one or more of the injection conditions reaching a threshold level;
        controlling the flow of the biomaterial in accordance with a second operating parameter during at least a portion of the curing of the flowable biomaterial in the intervertebral disc space, wherein the second operating parameter permits a portion of the flowable biomaterial to be expelled from the intervertebral disc space; and
    removing a delivery tube fluidly coupling the reservoir from the intervertebral disc space in response to at least partial curing of the biomaterial.

2. The method of claim 1 comprising the step of fluidly coupling the reservoir containing the flowable biomaterial to a mold located in the intervertebral disc space.

3. The method of claim 2 wherein the first operating parameter comprises delivering the flowable biomaterial to the mold so that the mold substantially fills the intervertebral disc space.

4. The method of claim 1 wherein the first operating parameter comprises delivering the flowable biomaterial at a pressure sufficient to distract the intervertebral disc space.

5. The method of claim 1 comprising the step of waiting a predetermined period of time after the at least one injection condition reaches the threshold level before initiating the second operating parameter.

6. The method of claim 1 wherein the step of controlling the delivery of the flowable biomaterial comprises a third operating parameter that maintains the flowable biomaterial at a predetermined pressure in the intervertebral disc space for a predetermined period of time.

7. The method of claim 1 wherein the second operating parameter delivers additional flowable biomaterial into the intervertebral disc space.

8. The method of claim 1 comprising the step of pretreating the flowable biomaterial.

9. The method of claim 1 comprising the step of exposing the flowable biomaterial to ultraviolet light and/or heating prior to delivery to the intervertebral disc space.

10. The method of claim 1 comprising the step of mixing the flowable biomaterials before they reach the intervertebral disc space.

11. The method of claim 1 wherein the flowable biomaterial comprises a plurality of components, the method comprising the step of mixing the components as they flow toward the intervertebral disc space.

12. The method of claim 1 comprising the step of directing the flow of biomaterial away from the intervertebral disc space until a predetermined quantity of biomaterial is delivered to a chamber in a purge device.

13. The method of claim 1 wherein the first operating parameter comprises the step of delivering the flowable biomaterial at a first operating pressure.

14. The method of claim 13 wherein the second operating parameter comprises the step of delivering the flowable biomaterial at a second operating pressure lower than the first operating pressure.

15. The method of claim 13 wherein the intervertebral disc space exerts pressure on the flowable biomaterial in the intervertebral disc space greater than the second operating pressure.

16. The method of claim 1 wherein the step of monitoring at least one injection condition comprises monitoring the pressure of the flowable biomaterial between the reservoir and the intervertebral disc space.

17. The method of claim 1 wherein the step of monitoring at least one injection condition comprises monitoring the pressure of the flowable biomaterial in the intervertebral disc space.

18. The method of claim 1 wherein the step of monitoring at least one injection condition comprises monitoring at least one of the pressure, the flow rate, elapsed time, or the total volume of the flowable biomaterial flowing between the reservoir and the intervertebral disc space.

19. The method of claim 1 wherein the first operating parameter comprises a first injection pressure of about 50 psi to about 270 psi.

20. The method of claim 1 wherein the second operating parameter comprises a second injection pressure of about 0 psi to about 150 psi.

21. The method of claim 1 wherein the threshold level of the injection condition is about 80 psi to about 150 psi.

22. The method of claim 1 comprising the step of recording data corresponding to one or more of the injection conditions during the flow of flowable biomaterial.

23. The method of claim 1 comprising the step of uploading to a computer data corresponding to one or more of the injection conditions recorded during the flow of flowable biomaterial.

24. The method of claim 1 comprising the steps of:
determining that the at least one injection condition comprises an out of specification condition; and
indicating an out of specification condition.

25. The method of claim 1 comprising the steps of:
determining that the at least one injection condition comprises an out of specification condition; and
altering the flow of flowable biomaterial to the intervertebral disc space.

26. The method of claim 1 comprising the steps of:
determining that the at least one injection condition comprises an out of specification condition; and
withdrawing at least a portion of the biomaterial from the intervertebral disc space.

27. The method of claim 1 wherein the flow of flowable biomaterial is manually switched to the second operating parameter in response to one or more of the injection conditions reaching a threshold level.

28. The method of claim 1 comprising adjusting the threshold level as a function of a size of a mold.

29. The method of claim 1 comprising adjusting the threshold level as a function of patient parameters.

30. The method of claim 1 wherein the first operating parameter comprises a plurality of variables.

31. The method of claim 1 wherein the second operating parameter comprises a plurality of variables.

32. The method of claim 1 comprising the steps of:
positioning an evaluation mold in the intervertebral disc space prior to the delivery of the biomaterial;
delivering a liquid to the evaluation mold so that the mold substantially fills the intervertebral disc space;
removing the liquid from the evaluation mold;
measuring the amount of liquid present in the evaluation mold; and
removing the evaluation mold from the intervertebral disc space.

33. The method of claim 32 comprising the step of delivering the liquid under pressure sufficient to distract the intervertebral disc space.

34. The method of claim 32 wherein one or both of the liquid and the evaluation mold have radiopaque properties.

35. The method of claim 32 comprising the steps of:
imaging the intervertebral disc space containing the evaluation mold and the liquid; and
establishing at least one of the first operating parameter and the second operating parameter based on the imaging of the intervertebral disc space.

36. The method of claim 32 comprising the steps of:
imaging the intervertebral disc space containing the evaluation mold and the liquid; and
measuring the distraction of the intervertebral disc space.

37. The method of claim 32 comprising the steps of:
imaging the intervertebral disc space containing the evaluation mold and the liquid; and
evaluating whether the mold substantially fills the intervertebral disc space.

38. The method of claim 32 comprising the steps of:
imaging the intervertebral disc space containing the evaluation mold and the liquid; and
evaluating a geometry of the intervertebral disc space.

39. The method of claim 32 wherein the evaluation mold is positioned in the mold.

40. The method of claim 32 wherein the evaluation mold is positioned in the intervertebral disc space before the mold is positioned in the intervertebral disc space.

41. The method of claim 32 comprising the steps of:
imaging the intervertebral disc space;
estimating the volume of biomaterial required to fill the intervertebral disc space; and
comparing the amount of liquid present in the evaluation mold with the estimated volume of biomaterial.

42. The method of claim 1 comprising the steps of:
positioning an evaluation mold in the intervertebral disc space;
delivering a liquid under pressure to the evaluation mold sufficient to distract the intervertebral disc space;
holding the volume of liquid in the evaluation mold constant for a period of time; and
adding additional liquid to the evaluation mold when the pressure in the mold drops to a predetermined level.

43. The method of claim 42 comprising repeating the steps of delivering, holding and adding additional liquid a plurality of cycles.

44. The method of claim 1 comprising the steps of:
positioning an evaluation mold in the intervertebral disc space;
continuously delivering a liquid to the evaluation mold at a constant pressure;
measuring the rate at which the liquid is delivered to the evaluation mold; and
estimating the compliance of the intervertebral disc space as a function of the changing rate at which the liquid is delivered.

45. The method of claim 1 comprising the steps of:
positioning a guide wire in the mold; and
imaging the intervertebral disc space containing the guide wire.

46. The method of claim 45 wherein the guide wire comprises an imaging target.

47. The method of claim 2 comprising the steps of:
positioning a radiopaque sheath over the mold before the delivery of the biomaterial;
imaging the intervertebral disc space containing the radiopaque sheath; and
removing the radiopaque sheath before delivering the biomaterial.

48. The method of claim 47 wherein the radiopaque sheath comprises at least one bend adapted to direct the mold to selected regions of the intervertebral disc space.

49. The method of claim 2 comprising the step of adding at least one bend to a delivery tube connecting the reservoir to the mold.

50. The method of claim 2 comprising the step of adding at least guide wire to a delivery tube connecting the reservoir to the mold.

51. A method of claim 1 wherein the intervertebral disc space includes an annulus with an inlet connected to a cavity formed therein, the method comprising the steps of:
inserting a delivery tube fluidly coupled to the reservoir into the cavity in the annulus; and
positioning a flange located on a distal end of the delivery tube against the inlet to the cavity.

52. A method of claim 1 wherein the intervertebral disc space includes an annulus with an inlet connected to a cavity formed therein, the method comprising the steps of:
inserting a delivery tube fluidly coupled to the reservoir into the cavity in the annulus; and expanding a distal end of the delivery tube against the inlet to the annulus in response to the delivery of flowable biomaterial.

53. A method of claim 1 wherein the intervertebral disc space includes an annulus with an inlet connected to a cavity formed therein and the method comprises the step of fluidly coupling a reservoir containing the flowable biomaterial to the cavity in the annulus.

* * * * *